US008753257B2

(12) United States Patent
Mersky

(10) Patent No.: US 8,753,257 B2
(45) Date of Patent: Jun. 17, 2014

(54) METHOD AND APPARATUS FOR ALIGNING ANTENNAS OF LOW-POWERED INTRA- AND EXTRA-ORAL ELECTRONIC WIRELESS DEVICES

(75) Inventor: Barry L. Mersky, Highland, MD (US)

(73) Assignee: Audiodontics, LLC, Bethesda, MD (US)

( * ) Notice: Subject to any disclaimer, the term of this patent is extended or adjusted under 35 U.S.C. 154(b) by 386 days.

(21) Appl. No.: 13/212,034

(22) Filed: Aug. 17, 2011

(65) Prior Publication Data

US 2012/0041298 A1   Feb. 16, 2012

Related U.S. Application Data

(63) Continuation-in-part of application No. 12/708,569, filed on Feb. 19, 2010.

(51) Int. Cl.
*G02C 11/06*   (2006.01)
*A61B 6/00*   (2006.01)
*A61B 5/055*   (2006.01)

(52) U.S. Cl.
CPC ............... *A61B 6/482* (2013.01); *A61B 5/055* (2013.01); *H04R 2460/13* (2013.01)
USPC ............................................ 600/25; 381/312

(58) Field of Classification Search
CPC .......... A61B 6/482; A61B 5/055; A61B 5/06; A61B 6/00; H04R 2460/13; H04R 25/554
USPC ............................................ 600/25; 381/312
See application file for complete search history.

*Primary Examiner* — Christine Matthews
*Assistant Examiner* — Joshua D Lannu
(74) *Attorney, Agent, or Firm* — William C. Schrot; AuerbachSchrot LLC

(57) ABSTRACT

A method and system of aligning antennas of an intra-oral and extra-oral electronic wireless device is provided. Three-dimensional anatomical data of at least a portion of an oral cavity of a subject and at least a portion of an external ear of the subject is recorded. A spatial relationship between a landmark in the oral cavity and a landmark in the external ear is determined. A first antenna is modeled based upon the anatomical data of the oral cavity, and a second antenna is modeled based upon the anatomical data of the external ear. The antennas are configured and oriented relative to each other for optimal signal transmission based upon the recorded anatomical data of the oral cavity and ear.

7 Claims, 14 Drawing Sheets

METHOD AND APPARATUS FOR ALIGNING ANTENNAS OF LOW-POWERED INTRA- AND EXTRA-ORAL ELECTRONIC WIRELESS DEVICES

CROSS REFERENCE TO RELATED APPLICATIONS AND CLAIM TO PRIORITY

The present application is a continuation-in-part of U.S. application Ser. No. 12/708,569, filed Feb. 19, 2010, the disclosure of which is incorporated herein by reference and to which priority is claimed.

FIELD OF THE INVENTION

The present invention relates generally to systems and methods for optimal placement of antennas in hearing augmentation transmitter and receiver assemblies, which antennas are elements in intra-oral to extra-oral (or visa versa) wireless electronic systems.

BACKGROUND OF THE INVENTION

Various designs exist for dental bone conduction hearing aid systems that use radio transmission of external ambient sound from an extra-oral device to an intra-oral device. Such devices function as receivers of radio frequency-modulated (FM) or amplitude-modulated (AM) transmission. For example, see U.S. Pat. No. 2,995,633 to Puharich; U.S. Pat. No. 5,447,489 to Issalene; U.S. Pat. No. 5,033,999 to Mersky; and U.S. Pat. No. 5,460,593 to Mersky.

Many devices rely on a "send mode" of transmitting non-acoustic signals recorded in the bone conduction pathway or through the body. For example, U.S. Pat. No. 6,823,195 to Boesen discloses ear microphones. U.S. Pat. No. 6,047,163 to Miyoshi discloses a miniature loop antenna placed on the wrist with the two antenna leads capacitively-coupled through the body. Other references describe tooth microphones from a first unit worn inside the mouth to a radio receiver second unit worn outside the mouth. For example, see U.S. Pat. No. 7,269,266 to Anjannappa. U.S. Patent Publication No. 2009/0022351 to Wieland et al. describe an inductive mode of "send" transmission of speech data from a tooth device having only a single receiving antenna, which responds to changes in the magnetic field created by movement of a magnet attached to a tooth. U.S. Pat. No. 6,394,969 to Lenhardt relates to a tinnitus suppressor and masker. U.S. Patent Publication No. 2009/0270673 to Abolfathi et al. relates to methods and systems for tinnitus treatment comprising an oral appliance having an electronic and/or transducer assembly for generating sounds via a vibrating transducer element. U.S. Patent Publication No. 2007/0280495 to Abolfathi et al. discloses methods and apparatus for processing audio signals. U.S. Pat. No. 5,447,489 to Issalene et al. relates to a hearing aid device comprising an extra-buccal wireless transmitter part and an intra-buccal wireless receiver transducer part for receiving signals from the transmitter part and comprising at least one vibrating element. U.S. Patent Publication No. 2009/0281433 to Saadat et al. relates to systems and methods for determining a pulmonary function by mounting one or more sensors intra-orally, capturing intra-oral data, and determining the pulmonary function based on an analysis of the intra-oral data. U.S. Patent Publication No. 2009/0274325 to Abolfathi relates to methods and apparatus for transmitting vibrations via an electronic and/or transducer assembly through a dental patch. U.S. Pat. No. 7,153,257 to Schneider et al. relates to an implantable hearing aid system that includes a transducer housing that is rotatable relative to a transducer mounting apparatus to orient the transducer for interfacing with an auditory component. Other devices transmit vibrations via an electronic and/or actuator assembly through a dental appliance.

Typically in dental bone conduction hearing aid systems, one antenna is located in the mouth, while the other external antenna is placed somewhere on the body. Conventional hearing aid systems are prone to decreasing and/or inefficient antenna placement and signal transmission, and inconsistent signal strength and clarity. In particular, if antennas are not optimally aligned, the power necessary for the signal transmission is overdone, and thus precious battery power is wasted. As a result, ease of use and efficiency of such conventional systems is degraded.

In conventional hearing aid systems, a variety of obstacles have thwarted the use of low-power radio and inductive signal transmissions to and from the human mouth. One such obstacle is the variability in the skull size, skull mass, and dentition. Further, the electrical charge of human skin and tissue creates interference to an internally disposed (in-mouth) antenna. Moreover, determining or measuring in-situ the actual strength of a low-power electromagnetic signal transmission to and from the mouth poses a technological challenge. In addition, slight movements of either the transmitting or receiving antenna during usage typically results in signal noise or degradation, thereby degrading optimal positioning of the antennas.

Thus, there is a need to establish a stable and repeatable co-location of an antenna of an extra-oral device relative to an antenna of an intra-oral device.

SUMMARY OF THE INVENTION

There is a need for an improved system and method for an in-mouth or intra-oral hearing aid system that achieves maximum antenna efficiency, repeatability of signal strength, clarity, and ease of use. With present wireless dental bone conduction systems, the power necessary for the signal transmission between an external transmitter and internal receiver is overdone and precious battery power is wasted.

The present invention relates to systems and methods for optimal placement of antennas in hearing augmentation systems including transmitter and receiver assemblies. Such antennas are elements in intra-oral and extra-oral assemblies which communicate wirelessly via signals. Systems related to the invention may transmit data via electromagnetic radio waves or through a magnetic field inductive coupling, including near-field and far-field magnetic coupling.

According to one aspect of the invention, a hearing augmentation system provides for stimulation to the inner ear via the dental bone conduction pathway when the system is operating in a "receive mode". According to another aspect of the invention, a "send mode" system transmits non-acoustic information or voice data from inside the mouth to a receiver located outside the mouth. It should be noted that the type and purpose of the data transmitted between the antennas (intra-oral and extra-oral) may vary.

According to another aspect of the invention, a hearing augmentation system includes transmitter and receiver assemblies having coupled antennas that are optimally designed and favorably aligned and oriented on the skull and/or head of a living person. Preferably, the assemblies are semi-rigidly affixed proximate to and/or against the head of the user, such as via a band or within a helmet or other head fixture. Accordingly, in some embodiments, the assemblies may not be in direct contact with the skull.

According to another aspect, the internal intra-oral antenna and the external extra-oral antenna of the corresponding transmitter and receiver assemblies are directional. The disclosed methods and systems for obtaining anatomical data of a user may be utilized to establish the design, shape, distance, and spatial and three-dimensional orientation of the antennas. Prior to designing the system of antennas, a technician can evaluate potential constraints caused by a user's unique physical and anatomical limitations. After evaluation, the technician can design the antennas and precisely match the antennas to a desired transmission band (AM, FM, Ultra Wide Band, Pulse-width, etc., including inductive coupling). Thus, this invention provides the technician the ability to evaluate a priori the spatial configuration of a specific human skull before designing the hearing augmentation receiver/transmitter system. The novel approach of precisely matching the antennas results in optimum gain, polarization, and overall signal transmission efficiency of the system, whether the system is "send-only," "receive-only" or a combination of "send-receive".

Accordingly, an apparatus and method are disclosed for co-locating and orientating a matching pair of directional antennas in wireless electronic signal transmission systems having a first unit worn inside the mouth and a second unit worn outside the mouth. An overall functional system requires both intra-oral and extra-oral units. As used herein, internal unit refers to a wireless intra-oral device and external unit refers to a wireless extra-oral device. Correspondingly, internal and external antennas are respectively affixed to the intra-oral and the extra-oral electronic devices, respectively.

According to one embodiment of a hearing augmentation system, the internal unit includes an internal "receive" antenna worn in the buccal space of a user's mouth, positioned lateral to the maxillary bicuspids and molars. The external unit includes an external antenna preferably worn on the same side of the head as the internal unit, most preferably attached to the pinna of the ear of the user, or worn in or on the external canal of the user's ear. Alternatively, the external unit may be worn at another location on the user's head and held firmly in place relative to the internal unit.

Anatomical data of the user's mouth and ear is collected prior to the design and alignment of the internal and external units. According to one embodiment, a hearing augmentation system utilizes two custom impressions made using novel impression trays—a mouth impression and an ear impression. From the mouth impression, a laboratory technician is able to create a dental cast or stone model of relevant portions of the mouth anatomy (such as done for various dental procedures). From the ear impression, the technician is able to create a cast of relevant portions of the ear anatomy (such as done when fabricating in-ear hearing aids). A mouth-ear alignment tool (described if further detail below), is then used by the technician to mount and orient the two casts. When the two casts are properly seated and secured to the mouth-ear alignment tool, the actual fabrication of the hearing augmentation system may be efficiently accomplished.

According to one embodiment, the mouth-ear alignment tool resembles in part a dental facebow. Historically in dental practice, a facebow has been used to transfer to a dental articulator apparatus the spatial relationship between the maxillary and mandibular arches and the tempromandibular joint. From recordation of this relationship, the patient's bite and oral anatomy can be recreated in the laboratory. Technicians then can fabricate a prior dental appliances that conform properly to the bite of the patient. In the present invention, a novel impression tray for the ear is utilized. A professional, such as a dentist, may take impressions of both the ear and the mouth, as opposed to an ear specialist taking an impression of the ear such as when custom fitting a hearing aid.

Thus, a hearing augmentation system is provided which allows for a customized external unit to be easily and optimally placed on or against the head of the user relative to the internal unit. Through the use of the two interconnected impression assemblies, a hearing augmentation system may be constructed which includes antennas that are optimally matched and aligned for a given application and with consideration for any anatomical constraints. For example, space limitations may dictate the battery size and power availability of the internal unit. Hence, with limited power available, the alignment of the antennas, and whether to use radio transmission versus inductive coupling, may be relevant considerations. Cosmetic considerations may also factor into the design and placement of the external unit. For some applications, regulatory restraints may dictate the transmission band available. For example, the configuration of the antennas may be determined by transmission frequency allowed by a particular regulatory agency. In embodiments for military operations where soldiers may be closely co-located and seek covert transmission or on-the-move usage, the overall system design and antenna selection must accommodate these specialized situations. Hence, application specific considerations may dictate the antenna design, which is efficiently achieved through the disclosed methods.

According to another embodiment, the relevant portions of user's oral and auditory anatomy are collected via imaging technology. The collected data may then be processed by associated computer modeling software to determine optimum antenna design, alignment, and placement of the internal and external units (and thus associated antennas), thus achieving the goal of low-power wireless transmission between the internal antenna and the external antenna. In particular, information collected by imaging devices is processed by the software to reconstruct the patient's anatomy, so that the orientation, design, and positioning of the external antenna and the internal antenna may be optimized based on known physical properties of the signal transmission (e.g., electromagnetic wave transmission) through the skull and head. Thus, based on gathered data corresponding to the three dimensional anatomical shape and spatial orientation of the oral cavity and external ear (which includes the auditory canal), the position and design of the internal receiver antenna may be determined for optimum performance relative to the position and design of the corresponding external antenna.

The low-powered transmitter signals of the instant wireless electronic system may be in any wireless form (e.g., magnetic inductive coupling, radio frequency, microwave, Blue Tooth band, RTM, etc.) for transmission to and from the internal unit.

In a preferred embodiment, two or more different types of mouth-safe materials are used to pot the internal unit and internal antenna and affix them in the mouth. The internal antenna itself is potted in a mouth-safe, non-toxic silicone, which, because of its chemistry, is thermally and electrically non-conductive with a high "Q" value. An exemplary fast-cure silicone adhesive suitable for use as a potting material is available from Nusil Technology LLC of Carpintina, Calif. (e.g., Med2-4013 silicone adhesive). Such potting material is advantageous compared to typical dental materials such as methacrylates or compounds that use ultra-violet or free-radical polymerization methods, because such typical dental materials cause electrical interference if used to directly pot a low-powered antenna. The reason typical dental polymers (e.g. methylacrylates, urethanes, etc.) cause radio interference may be because low levels of free radicals remain uncured in such typical dental polymers. Further, even typical conformation sprays and coatings recommended by manufacturers as methods of sealing antennas from moisture and dust have been shown to be inadequate (if not mouth unsafe) for the potting of the internal antenna. The remainder of the internal unit, including the portion which contacts the gingiva or teeth and which houses the control circuits and power supply, may be potted in typical dental materials such as urethanes, composites, nylons, thermoplastics, etc. These materials are needed to provide rigidity and hardness, and to pot in a safe manner the other electrical components of the internal system, such as the control circuit and batteries.

The power supply of the present invention may be a battery, either replaceable or permanent. Alternatively, the system may include a power supply that is charged by inductance via an external charger. The power supply may alternatively be charged via direct coupling to an alternating current (AC) or direct current (DC) source. Alternatively, the system may include a power supply that is charged via a mechanical mechanism, such as an internal pendulum or slidable electrical inductance charger, which is actuated via for example by motions of the jaw and/or movement for translating the mechanical motion into stored electrical energy for charging power supply.

The internal antenna may be either a "send" or "receive" type antenna, depending on the purpose of the associated unit or system. If the system is utilized as a hearing aid, then the internal antenna is a "receive" antenna. If the system includes other aspects, such as a tooth microphone to record breath or physiological sounds, then the internal antenna functions alternatively as a "send" antenna with respect to the coupled antenna pair. If the system is intended for two-way voice communication, then the internal antenna may function as both the "receive" and "send" antenna. In this situation, the voice communication system will be a half-duplex system given it may transmit signals in both directions, but only in one direction at a time (i.e. not simultaneously). In preferred embodiments, the distance between the internal antenna and the external antenna is less than six inches.

The internal antenna is preferably designed as a loop and disposable in the buccal space of a patient or user. As known in the art, the buccal space is the distendable area inside the cheek and laterally adjacent to the maxillary molars. The internal antenna loop may have any suitable diameter, but preferably does not exceed one inch.

It is not necessary that the paired internal and external antennas have the same radius, cross-sectional area, or design. Thus, the particular design and configuration of the external antenna may vary compared to that of the internal antenna. The particular design of the external antenna depends upon various factors, such as cosmetics, the specific band width of signal transmission, and the anticipated strength of the signal transmission. Thus, the two antenna designs can vary so long as their orientation is determined beforehand, and the internal and external units and their corresponding antennas remain fixedly disposed during usage.

Accordingly, the present invention provides for a methodology and an apparatus for optimal linear polarization of inside-mouth/outside-mouth directional antennas for low powered radio and magnetic induction transmission in wireless electronic systems, wherein the location and orientation of the internal antenna may be positioned and re-positioned with accuracy and consistency. The internal unit is located and retained in its proper position through precise mechanical attachment to the teeth, as well as additional oral structures (e.g. dental implants). It is understood by those of ordinary skill in the art that re-positioning of certain oral appliances, such as removable partial dentures with precision attachments, typically occurs to within less than 0.2 mm of variance over a several year period, even with daily usage by a person. Such will be the design of the internal unit of the present invention, and thus the spatial orientation of the internal antenna can be known and assured.

The present invention further provides a methodology and an apparatus for optimal directional pairing of inside-mouth/outside-mouth antennas for low powered radio and magnetic induction transmission in a wireless electronic system, wherein the location and orientation of the external antenna is determined through the use of a novel mouth-ear alignment tool. Positional retention of the external antenna can be achieved through one or any combination of methods to fit into or around the ear cartilage, or within the external canal of the ear. Further, skin tapes and adhesives, or spring pressure from waxes, gels, foams, straps of a helmet, ear-loops, ear-hooks, and other devices and methods can aid in the retention of the external unit.

The present invention further provides a wireless electronic system comprising an intra-oral directional antenna and a companion extra-oral directional antenna respectively affixed to a first intra-oral unit and a second companion extra-oral unit, wherein the intra-oral unit comprises a transducer(s) for transducing electrical energy to mechanical energy and vice versa, said intra-oral unit imparting low amplitude vibrations to teeth for conduction via the dental bone conduction pathway to the inner ear, or conversely transducing vibrations within said dental bone conduction pathway to electrical energy; said electrical energy is magnetically induced or electromagnetically transmitted by to and from the intra-oral antenna to the extra-oral antenna, and wherein said intra-oral and extra-oral antennas are stably, fixedly and spatially oriented relative to each other, a priori, for optimal gain and polarization.

As used in this specification, the transducer can be a device, usually electrical, electronic, electromechanical, electromagnetic, photonic, or photovoltaic that converts one type of energy or physical attribute to another for various purposes including measurement or information transfer. The transducer can also act as a sensor, used to detect a parameter in one form and report it in another (usually an electrical or digital signal), and can also act as an audio loudspeaker, which converts electrical voltage variations representing music or speech, to mechanical cone vibration and hence vibrates air molecules creating acoustical energy.

The wireless electronic system may receive incoming sounds either directly or through a receiver to process and amplify the signals and transmit the processed sounds via a vibrating transducer element coupled to a tooth or other bone structure, such as the maxillary, mandibular, or palatine bone structure.

In a preferred embodiment, the strength of the magnetic field transmitted to and from the companion antennas is less than or equal to 0 dBM. In yet another preferred embodiment, the intra-oral antenna is directly potted by medical grade silicone with a high "Q-value." In another embodiment, the chemically set silicone potting material is further encased by mouth safe polymers that contact the oral tissues of a person.

The present invention provides a dental bone conduction hearing aid comprising the wireless electronic system of the present invention, wherein the application of low-amplitude vibration to the teeth and conduction to the inner ear results in perception of speech.

The present invention further provides a method of treating or reducing the effects of motion sickness using the wireless electronic system of the present invention. The disclosed method comprises the application of low-amplitude vibration to the teeth, and conduction to the inner ear to treat or reduce the effects of motion sickness through cancellation of low frequency waves at the otolith.

Further, the present invention provides a method of treating or reducing stuttering using the wireless electronic system of the present invention. The method comprises the application of low-amplitude vibration to the teeth and conduction to the inner ear through a feed-back system, whereby the system is two-way send/receive which recognizes stuttering and sends blocking signal. In one embodiment, the wireless electronic system of the present invention can play a frequency shifted and delayed version of the sound directed at the patient, whereby the delayed playback stops or minimizes the patient's stuttering. For example, the sound is frequency shifted by about 500 Hz and the auditory feedback can be delayed by about 60 ms thereby reducing stuttering and producing speech more natural than without the system.

The present invention further provides a method of treating tinnitus using the disclosed wireless electronic system. As known in the art, tinnitus is a condition in which sound is perceived in one or both ears or in the head when no external sound is present. Such a condition may typically be treated by masking the tinnitus via a generated noise or sound. In one variation, the frequency or frequencies of the tinnitus may be determined through an audiology examination to pinpoint the range(s) in which the tinnitus occurs in the patient. This frequency or frequencies may then be programmed into the intra-oral device which is configured to generate sounds which are conducted via the user's tooth or bones to mask the tinnitus. One method for treating tinnitus may generally comprise masking the tinnitus, whereby at least one frequency of sound (e.g., any tone, music, or treatment using a wide-band or narrow-band noise) is generated via a transducer positioned against at least one tooth such that the sound is transmitted via vibratory conductance to an inner ear of the patient. The sound completely or at least partially masks the tinnitus perceived by the patient. In generating a wide-band noise, the sound level may be raised to be at or above the tinnitus level to mask not only the perceived tinnitus but also other sounds. Alternatively, in generating a narrow-band noise, the sound level may be narrowed to the specific frequency of the tinnitus such that only the perceived tinnitus is masked, and other frequencies of sound may still be perceived by the user. Another method may treat the patient by habituating the patient to their tinnitus where the actuator may be vibrated within a wide-band or narrow-band noise targeted to the tinnitus frequency perceived by the patient overlayed upon a wide-frequency spectrum sound. This wide-frequency spectrum sound, e.g., music, may extend over a range which allows the patient to periodically hear their tinnitus through the sound and thus defocus their attention to the tinnitus. In enhancing the treatment for tinnitus, a technician, audiologist, physician, etc., may first determine the one or more frequencies of tinnitus perceived by the patient. Once the one or more frequencies have been determined, the audiologist or physician may determine the type of treatment to be implemented, e.g., masking or habituation. Then, this information may be utilized to develop the appropriate treatment and to compile the electronic treatment program file which may be transmitted, e.g., wirelessly, to a processor coupled to the transducer such that the transducer is programmed to vibrate in accordance with the treatment program. Thus, in one embodiment, a method of treating tinnitus is provided using the disclosed wireless electronic system. The method comprises the application of low-amplitude vibration to the teeth and conduction to the inner ear by supplying a low-level "white noise" type of signal via the dental bone conduction pathway.

The present invention also relates to a wireless electronic system, wherein detection by a sensor such as tooth microphone of the low-amplitude vibration from the teeth or within the dental bone conduction pathway results in a signal that can be transmitted to a receiver unit worn outside the mouth. The receiver unit is capable of storing the transmitted data or further uplinking it to another system. The detection of the low-amplitude vibration from the teeth or within the dental bone conduction pathway can also result in a means for transmitting non-speech breath sounds to another listener or recording device for the measurement of pathological breath sounds. The pathological breath sounds can comprise any one of breath obstructions pertinent to the diagnosis of obstructive sleep apnea, respiratory conditions such as wheezes, or wales related to respiratory disease, speech impediments such as "low-voice", dysphonia, diseases and conditions related to the malfunctioning of vocal cords, or dysphagia and other problems related to swallowing.

The present invention also provides a wireless electronic system comprising a means for detecting skull vibration from the teeth or within the dental bone conduction pathway and transmitting the amplitude of the skull vibration to a human listener or recording device for determining whether there has been an abnormal skull acceleration or trauma, such trauma potentially damaging the brain.

The present invention further relates to a method of custom fit placement of an intra-oral unit in a wireless electronic system, said system comprising an intra-oral directional antenna and an extra-oral directional antenna respectively affixed to a first intra-oral unit and a second companion extra-oral unit wherein the intra-oral unit comprise actuators or transducers for transducing electrical energy to mechanical energy and vice versa, said intra-oral unit imparting low amplitude vibrations to teeth for conduction via the dental bone conduction pathway to the inner ear, or conversely transducing vibrations within said dental bone conduction pathway to electrical energy. The electrical energy is magnetically induced or electromagnetically transmitted by an intra-oral directional antenna and an extra-oral directional antenna. The intra-oral and extra-oral antennas are stably, fixedly and spatially oriented relative to each other, a priori, for optimal gain and polarization. The method comprises the steps of: stably and fixedly seating the intra-oral unit in a custom fit position on the maxillary arch; wherein a dental precision attachment means is used to maintain the stability of the intra-oral unit. Such means are known to artisans in the dental arts and readily available, such as from the "Precision Attachment Catalogue" issued by Sterngold, Inc. of Attleboro, Mass. The dental precision attachment means also can comprise customized claws and hooks that engage at least one tooth in said maxillary arch. The dental precision attachment means can also comprise a spring-loaded customized appliance, for example see appliances available from Valplast International Corp. of Oceanside, N.Y., that positions said intra-oral unit around teeth in the maxillary arch. The dental precision attachment means can also comprise oral denture adhesive applied to the polymer, resin, metal, or other dental material that contacts the soft tissue areas of the maxillary arch. Preferably, the dental precision attachment means comprise male-female components one of which is attached to at least one tooth or dental implant and are removably engageable to each other through friction-fit, press-fit or spring-force. The attachment means is used to position the intra-oral unit in the maxillary arch. In order to effectively transmit to the tooth or teeth the vibrations corresponding to the received auditory signals efficiently and with minimal loss of vibration transmission and/or sensation, secure mechanical contact between the actuator and the tooth is ideally maintained to ensure efficient vibratory communication. Accordingly, any number of mechanisms may be utilized to maintain this vibratory communication.

The present invention further relates to a method of spatial orientation a priori of an intra-oral directional antenna relative to an extra-oral directional antenna in a wireless electronic system. The system comprises an intra-oral directional antenna and an extra-oral directional antenna, which are respectively affixed to a first intra-oral unit and a second companion extra-oral unit. The intra-oral unit comprises actuators or transducers for transducing electrical energy to mechanical energy and vice versa. The intra-oral unit imparts low amplitude vibrations to teeth for conduction via the dental bone conduction pathway to the inner ear, or conversely transduces vibrations within said dental bone conduction pathway to electrical energy. The electrical energy is magnetically induced or electromagnetically transmitted by the intra-oral and the extra-oral antennas. The method comprises the steps of: making a custom maxillary arch impression on an impression tray to capture the anatomical details of a user's maxillary arch; optionally making a custom pinna and/or ear canal (ear) impression; determining the spatial relationship between the maxillary arch and the ear anatomy using an alignment tool; determining the optimal linear polarization between the intra-oral antenna and the extra-oral antenna on said impressions based on said spatial relationship; stably, fixedly, and precisely attaching the intra-oral and extra-oral antennas on the intra-oral and extra-oral units respectively; stably and fixedly seating said intra oral and extra oral units with said spatially oriented antennas in their respective custom fitting positions on the skull of said user.

The present invention further provides for maxillary arch and ear impressions made with non-toxic material such as polyvinlysiloxane, which can capture soft and hard tissue details with less than one percent distortion.

In one embodiment, a magnet of less than 2 mm in diameter is disposed on or about the intra-oral unit. Its planar alignment and center reflects the optimum transmission point of the intra-oral directional antenna as determined before the unit was placed into the mouth.

In another embodiment, the extra-oral directional antenna can be oriented in a direction designated by an alignment marker and determined by an apparatus adaptable for use with said alignment tool. The apparatus comprises an alignment marker and magnetic needles embedded therein. The needles are capable of aligning to a magnetic field emanating from the intra-oral cavity. The apparatus can point to the optimal orientation of an antenna located in the mouth. The optimal orientation is indicated by parallel alignment of the alignment marker to the magnetic needles. In one embodiment, the orientation of said oriented extra-oral directional antenna is held in place using means such as deformable semi-rigid tubing, skin tapes, waxes, ear hooks, or straps.

The present invention further relates to an alignment tool constructed to transfer to a location away from the face the spatial relationship between the maxillary arch and the ear anatomy. The tool comprises a means for anatomically simulated collocation of the maxillary arch impression and the ear impression. The alignment tool further comprises a mouth tray holding portion and an ear tray holding portion extendably joined at a disconnection sleeve wherein the mouth tray holding portion comprises an oral impression material holding tray, which may be pivotally (e.g., via a ball-joint) connected to the mouth tray holding portion. An ear tray holding tray is pivotally (e.g., via a ball-joint) connected to the ear tray holding portion. The tool is designed and configured to precisely align a user's maxillary arch impression with an ear, ear-hook, and/or ear canal impression. The mouth tray holding portion further comprises a laboratory stand mounting means for aid in remotely reproducing the anatomically simulated collocation of the oral impression and the ear impression.

In one embodiment of the alignment tool, the ear impression holding tray and the mouth impression holding tray are slidably connected to the ear tray holding portion and the mouth tray holding portion respectively via tray mounting means. Calibration scales are optionally provided along portions in slidable engagement with the tray mounting means. In another embodiment of the alignment tool, the disconnection sleeve comprises mate-able half-round members which extend from the ear tray holding portion and the mouth tray holding portions of the tool in an opposable manner. Retaining pins and opposed pin holes are provided for calibrated extension and disconnection of the ear tray holding portion from the mouth tray holding portion.

This invention also provides an otoblock device adaptable for use in the alignment tool comprising a thin deformable wire intertwinable with a fine mesh material. The device comprises on one terminal end a mesh-work for use as an otoblock during ear impression taking, and on the other terminal end, a precision block which is fixably and rigidly connected to the ear tray holding portion of the alignment tool.

In one embodiment, a non-magnetic apparatus adaptable for use in the alignment tool is provided in lieu of the ear impression tray. The apparatus comprises an alignment marker and magnetic needles embedded therein. The needles are capable of aligning to a magnetic field emanating from intra-oral cavity, wherein said apparatus can point to optimal orientation of an antenna located in the mouth. The optimal orientation is indicated by parallel alignment of the alignment marker to the magnetic needles.

The methodology of the present invention is easily adaptable to a situation where more than one intra-oral unit is desired. For example, multiple transducer assemblies may be placed on multiple intra-oral units. Although they are typically mounted on the upper row of teeth, multiple intra-oral units may alternatively be positioned and located along the lower row of teeth or both rows as well. Moreover, each of the transducers may be configured to transmit vibrations within a uniform frequency range. Alternatively in other variations, different intra-oral units may be configured to vibrate within non-overlapping frequency ranges between each unit. As mentioned above, each transducer can be programmed or preset for a different frequency response such that each transducer may be optimized for a different frequency response and/or transmission to deliver a relatively high-fidelity sound to the user.

Thus, the present invention relates to directional antennas, and mechanisms and methods for their optimal design, alignment, orientation, and affixed positioning on the skull and/or head of a living person. The antennas are paired-elements in an ear-level and intra-oral wireless electronic system that function, in one embodiment, as a dental bone conduction hearing aid. The antenna pair transmits data via electromagnetic radio waves, or through magnetic induction coupling.

In some embodiments, software and imaging technologies are utilized which: (1) Measure and record in 3-D the anatomical and spatial relationship between landmarks within the oral cavity and landmarks in or near the ear canal; (2)

Determine the anatomical volume of those two cavities, and then model the optimum size and shape of an antenna pair that can fit within or in proximity to the cavities; (3) Determine the optimum configuration of the antenna pair based upon the transmission carrier-frequency band and with consideration to the theoretical and known interactions of the signal with the different skull and/or head tissue medium (e.g., water, muscle, bone); (4) Determine the best fixation means and position within or proximate to the two cavities; and (5) Determine the in-situ tilt or 3-D spatial orientation of each antenna in the pair so that the electrical (battery) power required of the system is at a minimum when: (a) The transmission signal has its greatest signal-to-noise ratio (SNR), and (b) the SNR remains repeatable after removing and replacing the transmitter/receiver on the skull and/or head. In one embodiment, a hearing augmentation system provides stimulation to the hearing nerve via the dental bone conduction pathway (hearing aid).

According to one embodiment, a method of aligning antennas of an intra-oral and extra-oral electronic wireless device comprising the steps of: recording three-dimensional anatomical data of at least a portion of an oral cavity of a subject; recording three-dimensional anatomical data of at least a portion of the external ear (which includes the auditory canal) of the subject; determining a spatial relationship between a landmark in the oral cavity and a landmark in or proximate to the external ear; modeling a first antenna based upon the anatomical data of the oral cavity; and modeling a second antenna based upon the anatomical data of the external ear, wherein the first and second antennas are configured and oriented relative to each other for optimal signal transmission based upon the recorded anatomical data of the oral cavity and external ear.

An imaging device may be utilized to record the anatomical data during said recording steps. The imaging device may be one of an ionizing radiation system or a non-ionizing system. For example, the imaging device may be a two or three-dimensional X-ray imaging system, a cone beam computed tomography imaging system, a magnetic resonance imaging system, or an optical imaging system. Such an optical system may be based on laser optics, or alternatively, based on infrared, ultraviolet, or some other optical imaging system known in the art.

According to one aspect, the imaging device further records an anatomical volume of the oral cavity and an anatomical volume and shape of the external ear. An internal antenna is then modeled for disposing within the oral cavity of the subject based upon the determined recorded anatomical data of the oral cavity, and an external antenna is modeled for disposing within or near the external ear of the subject based upon the determined recorded anatomical data of the external ear. The internal unit is configured to be disposed within the oral cavity of the subject, the first antenna being coupled to the internal unit. An external unit is configured to be disposed within or near the external ear of the subject, the second antenna being coupled to the external unit. The first and second antennas are fixedly and spatially oriented relative to each other for optimal gain and polarization when the internal and external units are disposed within or upon the subject.

According to one aspect, the first antenna has a first angular orientation, and the second antenna has a second angular orientation relative to the first angular orientation. Signal transmission is optimized when the first and second antennas are orientated in the first and second angular orientations, respectively.

The present invention also relates to a system for aligning antennas of an intra-oral and extra-oral electronic wireless devices. The system includes a means for recording three-dimensional anatomical data of at least a portion of an oral cavity and at least a portion of an external ear of the subject, and means for processing the recorded anatomical data that determines a spatial relationship between a landmark in the oral cavity and a landmark in the external ear.

The means for recording may be one of an ionizing radiation imaging system or a non-ionizing imaging system. The means for processing may also determine an angular orientation of the landmark in the oral cavity relative to the landmark in the external ear. The landmarks are removable from the subject, and the system may further comprise a holding mechanism for spatially maintaining the removed landmark from the oral cavity and the removed landmark from the external ear.

The present invention is also directed to an apparatus for aligning antennas of an intra-oral and extra-oral electronic wireless devices. The apparatus includes an oral dummy unit including a first landmark, and an ear dummy unit including a second landmark. The oral dummy unit is configured for being positioned within an oral cavity of a subject and detected by an imaging device. The ear dummy unit is configured for being positioned within or proximate to an external ear of the subject and detected by the imaging device.

In one embodiment, the apparatus includes an imaging system for determining a spatial relationship between the first landmark and the second landmark. The imaging system may be one of an ionizing radiation system or a non-ionizing system. The imaging system further determines an angular orientation of the first landmark relative to the second landmark.

In one embodiment, the apparatus also includes an alignment mechanism, such as a bar or L-shaped rod or member, which includes a first end portion configured to releasably secure the oral dummy unit and a second end portion configured to releasably secure the ear dummy unit. The spatial relationship between the first landmark and the second landmark is maintained when the oral dummy unit and the ear dummy unit are secured to the alignment mechanism.

BRIEF DESCRIPTION OF THE DRAWINGS

In the drawings, wherein like reference numerals identify similar elements of the various embodiments.

DETAILED DESCRIPTION OF THE INVENTION

The "dental bone conduction pathway" may be considered a sub-pathway of the widely recognized non-acoustic "bone conduction pathway" for sound transmission to the hearing nerve. As used in this invention, the "dental bone conduction pathway" is distinguished from the "bone conduction pathway" in that sound perceived at the hearing nerve originates in structures of the mouth and pharynx. Speech sounds and chewing sounds, for example, travel to the hearing nerve via the dental bone conduction pathway. By contrast, loud ambient helicopter-like noises that penetrate the skin over the entire skull, neck, and body and can be considered noises arriving at the hearing nerve via the bone conduction pathway. Similarly, standard bone conduction audiometry with skull stimulation at the mastoid or forehead uses the bone conduction pathway. The distinction between pathways is important because of anatomical differences between the pathways. The bio-mechanical forces in the dental bone conduction pathway are variable and thus may create variable results when compared to stimulation of structures elsewhere on the skull (at the mastoid or forehead for example).

The large resonant chamber, anatomically named as the mouth and oropharynx, has its resonance frequency altered by combinations of opening the mouth and movements of the tongue, lips, and vocal chords (human speech). Other pathway entrances on the skull do not contain such compliant muscles and ligaments (except in the middle ear—although whether the middle ear can be considered "an entrance point" to the bone conduction pathway is an academic question). Also, those other skull areas have far less voluntary muscle and compliant soft tissue when compared to the tongue and cheeks of the mouth for example, and more fixed chambers (e.g., frontal sinuses, mastoid air cells, external ear canal), and thus necessarily have more consistent volumes, mechanical loads, and input mechanical point impedances than do structures of the mouth and pharynx; that is, structures comprising the dental bone conduction pathway.

Figure 1:
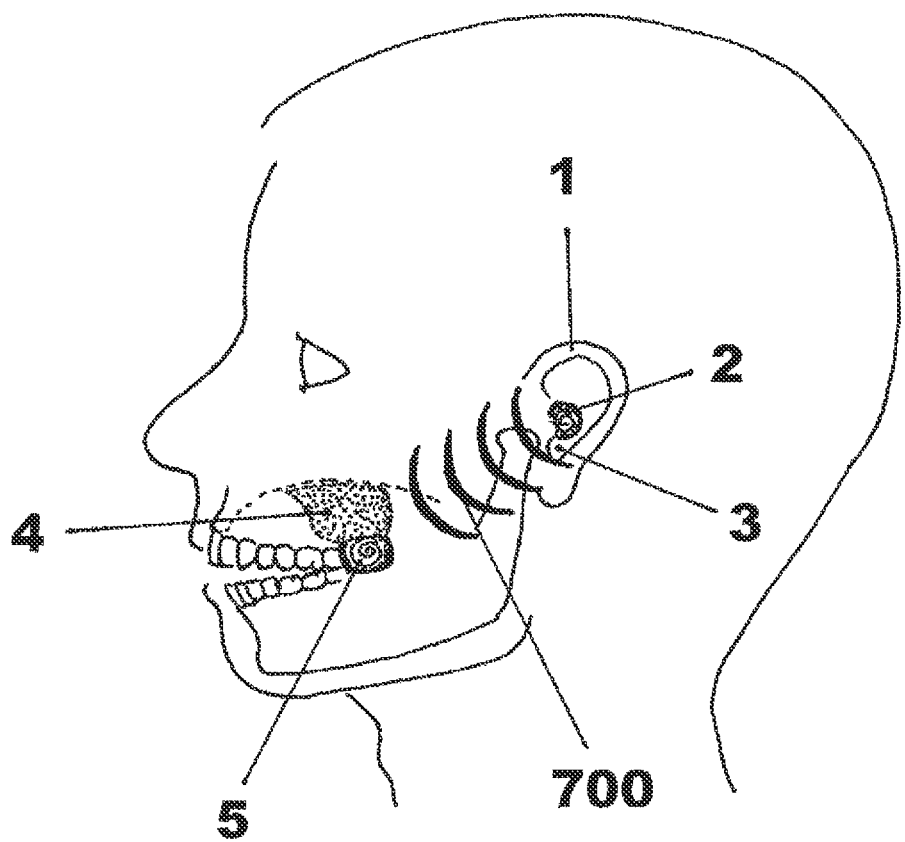
FIG. 1 illustrates an overall system view according to a typical embodiment of the invention.
Figure 2:
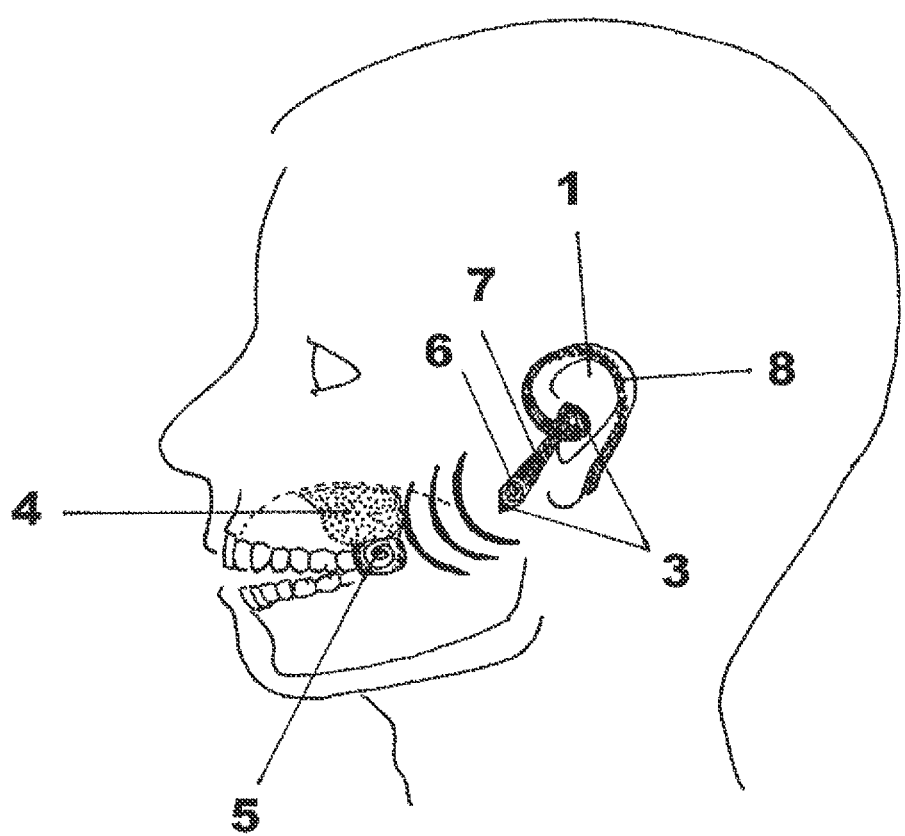
FIG. 2 illustrates a Hearing Aid System (Receive Mode) according to one embodiment of the present invention.
Figure 3:
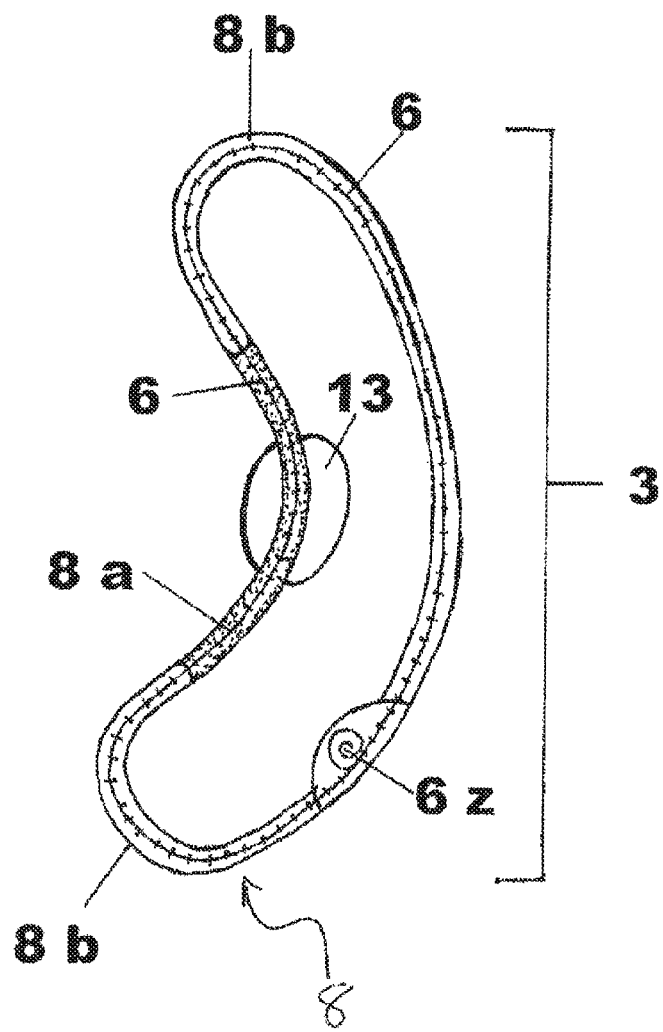
FIG. 3 illustrates another embodiment of the external unit.

Referring now to the drawings of the present disclosure in which like numbers represent the same structure in the various views, FIG. 1 illustrates an overall system view of a low powered transmission 700 from the external unit 3 to the internal unit 4 and vice versa according to an embodiment of the invention. The external unit 3 contacts either the tissue of the pinna 1 or external ear canal 2. The antenna element from the external unit 3 is not shown in FIG. 1 as it is internally placed within the cartilaginous external ear canal 2. Other placements of the extra-oral antenna element are shown in FIGS. 2 and 3. The internal unit 4 placed in the mouth comprises an antenna 5 preferably potted in silicone. In the preferred embodiment the intra-oral antenna 5 is disposed in the buccal space area of the mouth.

FIG. 2 illustrates a Hearing Aid System (Receive Mode) according to another embodiment of the present invention. In this embodiment an impression has been taken of the ear canal 2 using an ear impression tray 190 (shown in FIG. 7). The retention of the external unit 3 occurs through customization of the housing to the ear canal 2 by a laboratory technician. Depending on the depth of penetration within the ear canal 2, this housing is further depicted as components 13 or 14 in FIG. 6. Referring again to FIG. 2, the external antenna 6 is shown as being a loop antenna which would be a preferred design if the signal transmission means is inductive coupling. However, other antenna configurations could be used if the anatomy, space, transmission band or intended function, indicate that a different antenna design or configuration would be more efficient. The external unit 3 further comprises a connecting wire 7 to the other components of the external unit and an additional retaining feature 8, which in this Figure is an ear-loop.

The signals transmitted may be received by electronics and/or transducer assembly via a receiver, which may be connected to an internal processor for additional processing of the received signals. The received signals may be communicated to the transducer, which may vibrate the tooth to conduct the vibratory signals through the tooth and bone and subsequently to the inner ear to facilitate hearing of the user. The transducer may be configured as any number of different vibratory mechanisms. For instance, in one variation, the transducer may be an electromagnetically actuated actuator such as would be the case with a magnetostrictive material as a core. In other variations, the actuator may be in the form of a piezoelectric crystal having a range of vibratory frequencies, e.g., between 250 to 20,000 Hz.

The spatial location of the external antenna 6 along the cheek is not random, but was determined a priori by a technician using the mouth-ear alignment tool 100, described in further detail below. With use of tool 100, the laboratory technician analyzed several factors including the potential retention sites for the external unit 3. In this example, the technician decided that for comfort, ease-of-use, etc, an ear-loop in combination with natural retention provided by cartilaginous folds of the ear, retention and unit rigidity could be achieved so that the external unit 3 maintains the alignment/orientation of the external antenna 6 relative to internal antenna 5.

FIG. 3 illustrates another embodiment of the external unit 3. In this embodiment, the retention features of the external unit 3 can be considered as self-customized. By "self-customized," spring-loaded or foam earplugs (e.g., see Sony Sport Headphones Model MDRAS20J) may be combined with an ear-loop to create a stable and non-moving appliance that can be worn in the ear for extended periods and during active movement. In this embodiment, a novel method is employed by the user to locate the internal antenna 5 of the internal unit and determine its optimum "directionality." Without the instant invention, the user would need a "trial by error" method of moving the external unit 3 and external antenna 6 until it "seems OK". In this embodiment, the pointer 400 (See FIG. 11) on the alignment tool helps the user locate the internal antenna. Once the optimum orientation is shown by the pointer tool 400, the external unit 3 and external antenna 6 can be tilted or oriented to properly match the directionality of the internal antenna 5. It is anticipated that through everyday usage of the external unit 3, the user will soon adapt and learn how the unit feels and fits into or about their ear. Thus if during usage the unit moves, it is expected that by having learned how the unit should feel in one's ear for optimum signal transmission, the user will recognize that a misfit has occurred, and the antennas therefore are no longer optimally aligned.

The optimal a priori alignment of the external antenna 5 and the internal antenna 6 is important particularly when the system is being used in "send" mode or transmit-mode, such as would occur if the internal unit 4 was a tooth microphone or a tooth sensor. In such applications that wirelessly transmit speech or physiological data from inside the mouth without a side-tone supplied to the ear (and the normal ability to hear it), it is difficult for the user to know when the two antennas 5 and 6 have become misaligned and are not optimally transmitting a signal. By contrast, in "receive" mode (i.e. a hearing aid or device utilized as a listening unit for voice communication), there is a higher likelihood that the user can become aware of antenna misalignment because he will hear a "fuzzy" or distorted signal. In the "send-mode" without a side-tone feature, the user has no way of knowing whether the antennas were originally set properly or verifying during usage whether the antenna (5 and 6) remain properly aligned.

In FIG. 3, the self-customized retaining ear-loop 8 has associated with it a wrapped wire external antenna 6. In this embodiment, the ear-loop 8 has a metal spring tube 8a and rubber or silicone tube 8b that surrounds and goes behind the pinna 1. In this example, the metal spring tube 8a provides stability and retention to the external unit 3 by exerting a force directed medially (into the ear) on the conformation self-customized plug 13, and on the spring-like rubber (or other material) tube 8b. To customize this embodiment the user squeezes and conforms this deformable metal spring tube 8a to optimally align the external antenna 6 as shown through use of the pointer 400 (see FIG. 11). The wrapped wire antenna 6 is shown as running inside the tube 8a and 8b and has additional turns in the area 6z. Elements 6 and 6z are just one of many possible configurations for this external unit antenna design.

Figure 5:
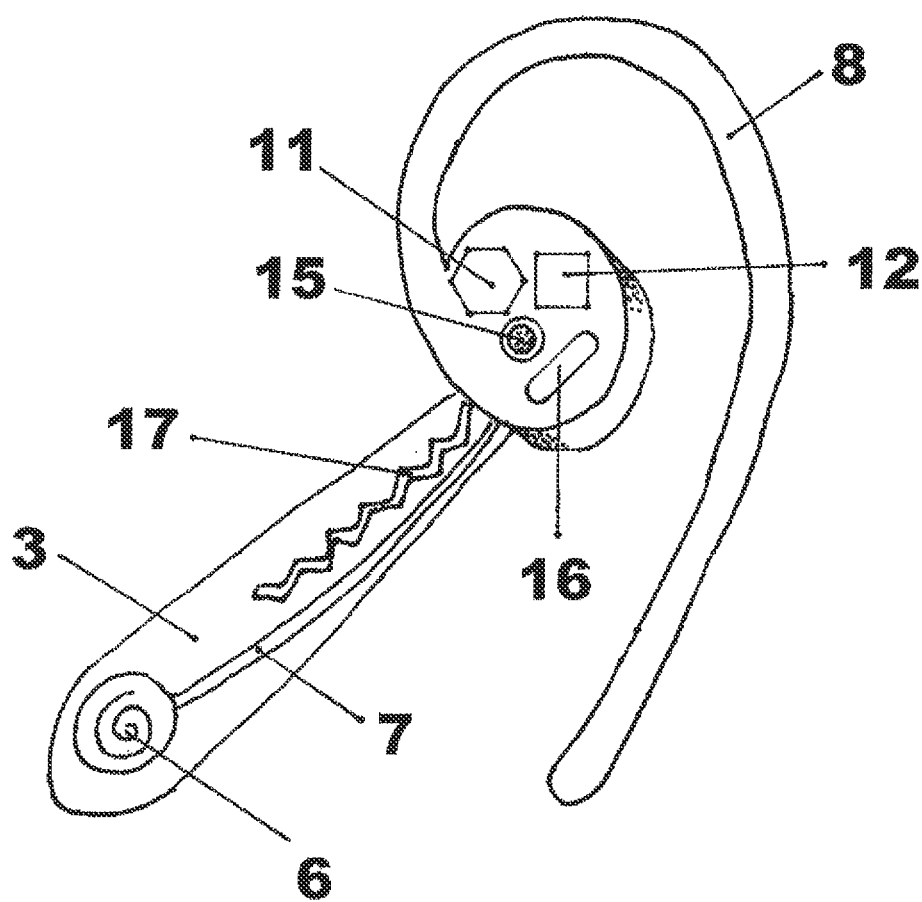
FIG. 5 illustrates another embodiment of the external unit with data logger/transceiver and two antennas.

Additional stabilization of the external unit 3 can be provided by a self-customized ear-plug like housing 13 (see FIG. 6) which may further comprise a vent or hole 15 (See FIG. 5). The vent allows acoustic information to pass unimpeded to the eardrum, and as an example, musicians' earplugs have a vented design. The vent 15 allows the user to experience near normal hearing, which is valuable or perhaps required for certain "send mode" applications in the military.

The positioning and orientation of the extra-oral antenna can be maintained through use of medical-grade adhesive tape, or from straps or spring-like pressure created by a helmet, hat, or other convenience worn on the skull. In applications such as for the military, once the optimal position for the external antenna 6 has been determined, helmet straps can be adjusted to further stabilize the positioning of the external unit 3 and external antenna 6. Alternatively, if the application is for the wireless transmission of physiological (non-acoustic) data from the internal unit, a means such as skin tape 18 can be used to secure the antenna is its proper orientation. Different means and methods can be used to secure the external antenna 6 in this self-custom embodiment, once the optimal position of the external antenna 6 relative to the internal antenna 5 has been determined through the understanding of the mouth-ear facebow 100, the pointer 400, and other teachings of this invention.

Figure 4:
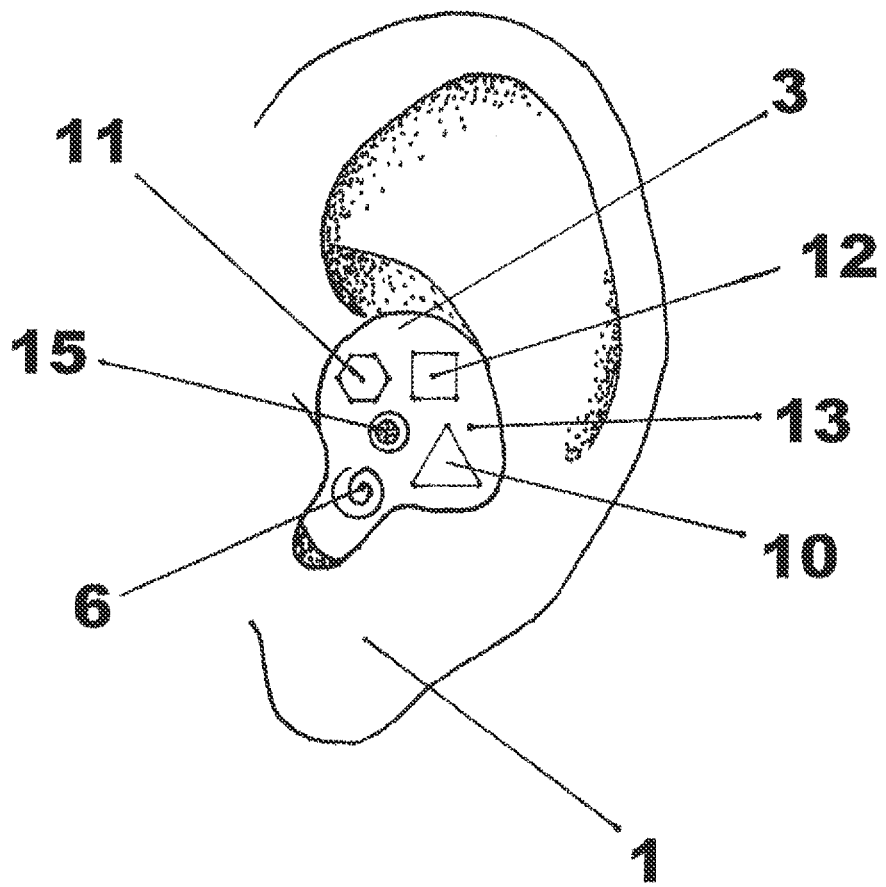
FIG. 4 illustrates a preferred embodiment of the external unit of a Hearing Aid System with microphone (Receive mode).

FIG. 4 illustrates a preferred embodiment of the external unit of a Hearing Aid System with microphone operating in a receive mode. In this embodiment, an ear impression has been made using other elements of the invention, namely the ear tray 190. The external unit 3 is seated partly into the pinna 1 and continues into the external ear canal 2. Specifically since this is a "Receive Mode" system, the external unit 3 comprises a microphone 10 to capture ambient acoustic information (speech, music, noise, etc.), a power supply 11, control circuit or processor 12, connecting wires (not shown), and a transmitting external antenna 6 for transmitting the processed signals to the intra-oral unit. In this embodiment, the external unit 3 transmits to the internal unit 4. The microphone 10 and processor 12 may be configured to detect and process auditory signals in any practicable range, but may be configured in one variation to detect auditory signals ranging from, e.g., 250 Hertz to 20,000 Hertz. Placement of the microphone 10 in the pinna or external ear canal is the preferable location for a hearing aid device because this location captures the most "natural sounds" caused by the shape and folds of the pinna of the ear.

With respect to microphone 10, a variety of various microphone systems may be utilized. For instance, microphone 10 may be a digital, analog, and/or directional type microphone. Such various types of microphones may be interchangeably configured to be utilized with the assembly, if so desired.

The microphone and processor may be configured to detect and process auditory signals in any practicable range, but may be configured in one variation to detect ambient auditory signals ranging from, e.g., 250 Hertz to 20,000 Hertz. The detected and processed signals may be amplified via amplifier, or processed through other digital processing means (DSP) known to those schooled in the art of audio signal processing and DSP. The effect of such DSP may be to increase the output level of the vibrational transducer of the internal unit 4, with such an increase being perceived as an increase in gain or loudness. Through signal compression, gating, etc., other audio effects can be processed by 12 prior to transmission from the external unit 3 to the internal unit 4.

As known in the art, when the ear canal 2 is occluded there is a "boost" in lower frequency sounds, particularly those created in the canal 2 by the bone conduction pathway. The external unit 3 of FIG. 4 further comprises a vent 15 which would not be necessary if the hearing aid system was for an individual with single-sided deafness because this ear would be "dead". If, however, the system application is to provide hearing via the dental bone conduction pathway to those individuals with high frequency sensorineural hearing loss, then a vent in this external unit would be appropriate.

FIG. 5 illustrates another embodiment of the external unit with data logger/transceiver and two antennas. This Figure presumes that the overall system is in "send mode" wherein the internal unit is functioning as a "tooth microphone" or sensor. Since this embodiment is presumed to be a "send-mode" external unit, a vent 15 is provided should the user have normal hearing. This vent functions similarly to the vent of FIG. 4 in that it allows ambient acoustic information to pass into the ear canal while at the same time, reducing the "occlusion effect" well known to artisans of air conduction hearing aids. Unlike the external unit 3 of FIG. 4, the external unit 3 of FIG. 5 does not contain a microphone, but rather comprises a data logger chip or transceiver 16. This chip captures the data from the internal unit 4 and either stores it to be downloaded by other means, or perhaps in real-time further transmits it to another remote storage unit via linkage with a computer or cell-telephone. Such transmission to a cell phone can occur through a secondary antenna 17, which may be tuned to a "Blue-Tooth" network, for example.

It is to be understood that this invention is not limited in any way by the purpose, mode of operation or the type of data transmitted to or from the internal unit 4 to the external unit 3 or how such data may be uplinked, saved, or otherwise connected to other systems for different purposes so long as the methodology of the present invention is utilized to optimally collocate the internal antenna 5 with the external antenna 6 particularly in a low-powered system.

Figure 6:
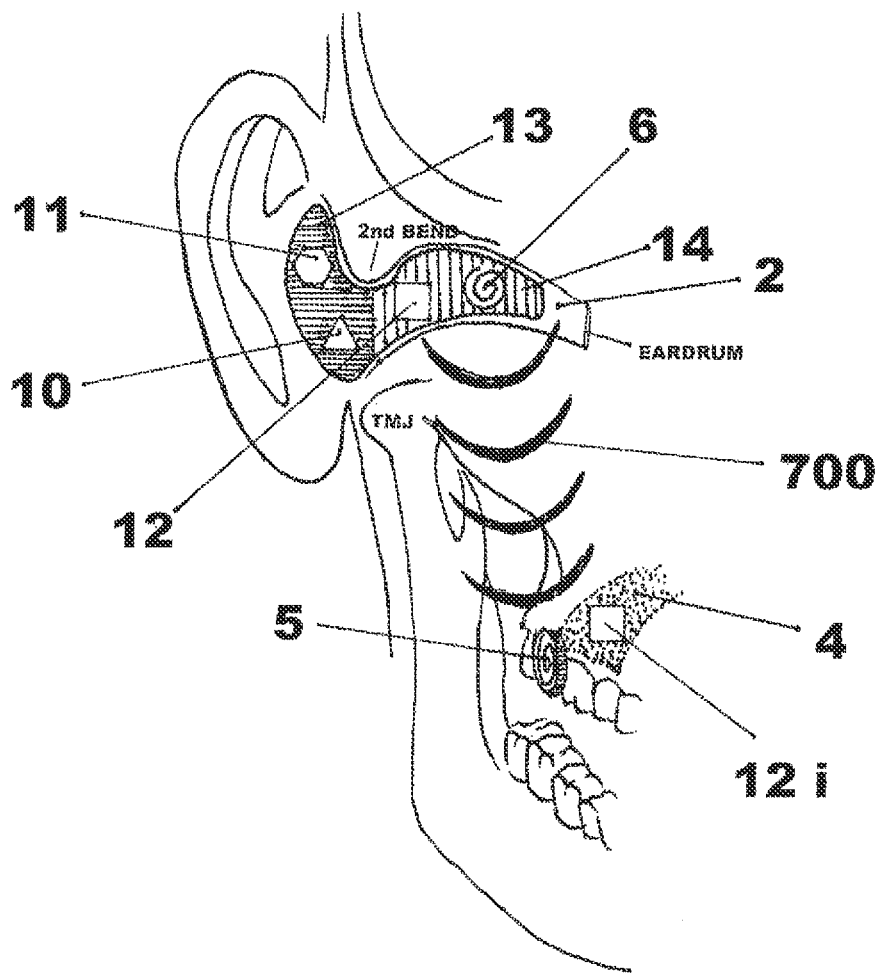
FIG. 6 illustrates an ear canal view of one embodiment of the external unit.

FIG. 6 illustrates an ear canal view of a hearing aid system wherein the housing of the external unit 3 extends from the pinna 1 to include the second bend in the external ear canal 2.

Additionally, the housing of the external unit may extend further down the external ear canal 2 just medial to the second bend. In FIG. 6, element 13 indicates portions of the housing of the external unit 3 extending through the second bend of the pinna and element 14 indicates portions of the housing extending just medial to the second bend. This distinction is made because ear impressions taken for the fitting of custom hearing aids or earplugs typically go just medial to the second bend. This has been shown to provide sufficient retention of "in the ear canal" type hearing aids and plugs.

The volume of the housing of the preferred embodiment shown in FIG. 4 is represented by the anatomical area described by element 13. It is possible, however, as advances in miniaturization are made in electronics, power supply, etc., that all electronic components for an external unit 3 of a hearing aid area may fit within element 14. In one embodiment of the present invention, the external antenna 6 may be located in housing area defined by element 14 as it may present a more favorable position for the external antenna 6 relative to the internal antenna 5.

FIG. 6 further shows the spatially close anatomical relationship between the buccal space of the mouth and the external ear canal. In this example, due to the physical proximity of the area of element 14 to the buccal space, the transmitting antenna 6 is shown disposed in the external canal approximately 2 mm away from the eardrum. It is transmitting through cartilage and bone to the internal unit 4 and its antenna 5, which is disposed in the buccal space lateral to a maxillary molar. Also shown in the internal unit 4 is a control circuit 12i which functions as an electronic controller for that distinct unit.

Figure 7:
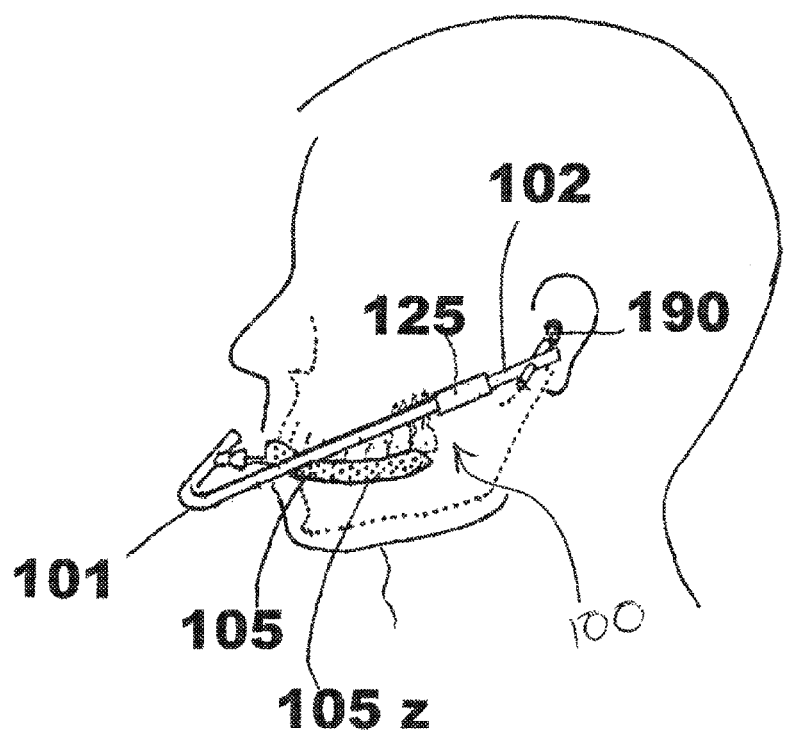
FIG. 7 illustrates a mouth-ear alignment tool in-situ.

FIG. 7 illustrates a novel mouth-ear alignment tool 100 in-situ. As used in this specification, a facebow is an alignment tool, means or apparatus to be used on the skull of a living person for recording the spatial relationship between the anatomy of the ear and the anatomy of the mouth in a manner that is reproducible remote from the skull. The said alignment means is also capable of recording the spatial relationship between at least one tooth in the mouth of a person and ear of that person in order that the positioning of an electronic device that produces or emits magnetic fields or electromagnetic waves from (or to) a device placed inside the mouth can be optimally disposed outside the mouth relative to the device worn inside the mouth, so that the alignment results in the lowest achievable wireless signal transmission power between the two units or devices.

Figure 8:
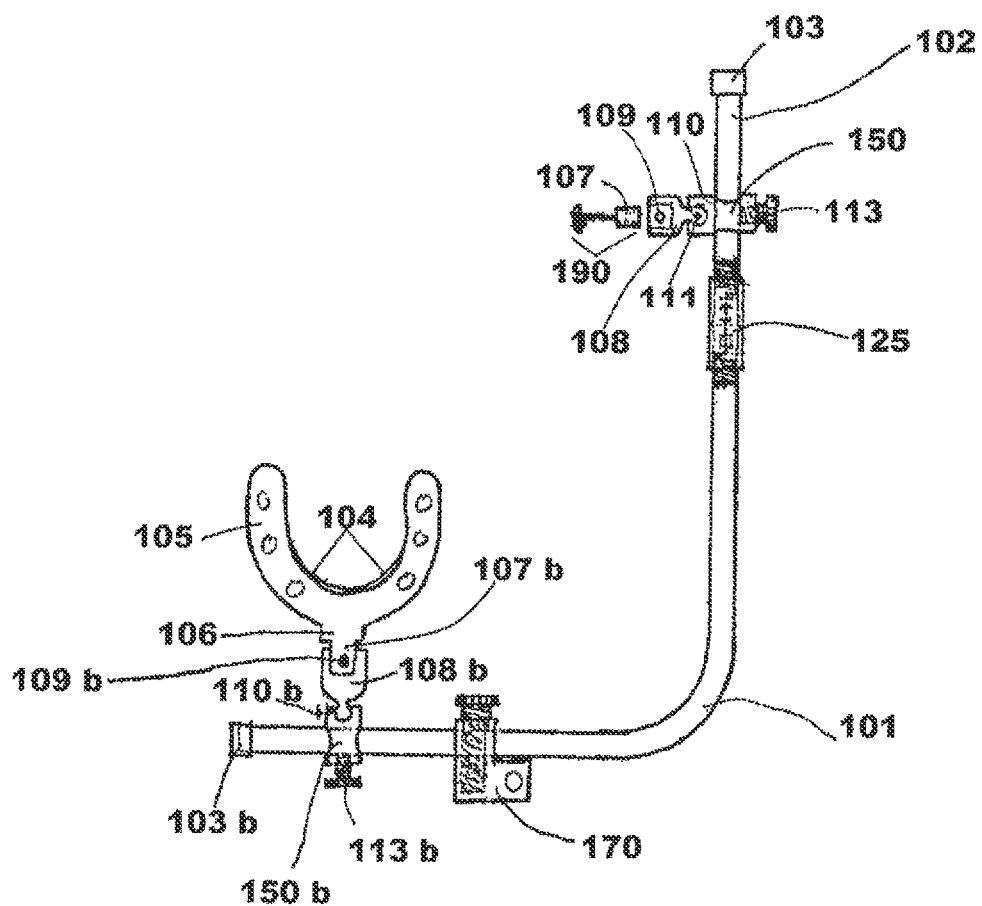
FIG. 8 illustrates a mouth-ear alignment tool according to one embodiment of the present invention.

Referring to FIGS. 7 and 8, the alignment tool 100 comprises a mouth tray holding portion 101 and an ear tray holding portion 102 joined at a disconnection sleeve 125. The alignment tool is preferably L-shaped. The mouth tray holding portion 101 comprises a tray or holder 105 for holding the impression medium 105z and means 150b to mount it to the portion 101. The impression medium can be any suitable material used in the art including but not limited to waxes, polyvinylsiloxanes, polyethers, waxes, compounds, plaster of paris. In a preferred embodiment, the tray 105 has walls or flanges 104 which serve to hold the impression material 105z in the tray 105. However, tray 105 need not have such walls 104 because other means and methods can be used to hold impression material 105z onto the tray 105. For example, the tray can be flat and yet have mesh and adhesive. It can be perforated, have small retentive grooves or a variety of designs so long as it can hold an impression medium 105z in a manner that records the anatomy of teeth and serve as an index of the anatomy. When the tray 105 and the impression material 105z are removed from the mouth, a stone or composite cast is poured from the impression and sent to a dental laboratory. At the laboratory, the stone cast is re-seated into material 105z that now serves as the orienting index for the stone cast. This methodology to "re-mount" and index this mouth-cast is well-known by dental laboratory technicians who articulate dental casts and fabricate dental appliances.

The method for obtaining the indexing or final impression of the mouth may be performed using conventional dental techniques. The tray 105 is available in different sizes, as is common in the dental art. The tray is intended to fit the maxillary or top dental arch. The trays 105 are available as separate and possibly disposable items. In a preferred design, the tray 105 connects to the mouth-tray holding portion of the alignment tool 101 via a two-step connecting handle 106 and 107b. 107b is similar in shape to handle element 107 of the ear impression tray 190. The two-steps (106 and 107b) are needed because the handle 106 of the mouth impression tray is larger than the handle 107 of the ear impression tray. Since the female receptacle 108b is intended to be similar to (ear) receptacle 108, a "step-down" is required.

The connecting means 107 and 107b are sized and configured to fit snuggly into female receptacle 108 and 108b which in turn are ball-jointedly connected to the respective tray mounting means 150 and 150b in contact with the ear and mouth tray holding portions respectively of the alignment means 100. The tray mounting means 150 and 150b are secured on the alignment means 100 by tightening screws 113 and 113b respectively.

This mouth impression, like the ear impression to be described below, stays unattached to the alignment tool until both impressions (mouth and ear) have been completed. It ultimately will be joined to the alignment tool through a ball-joint connection 108b (or other retaining mechanism) and secured with a tightening screw 109b.

Figure 9:
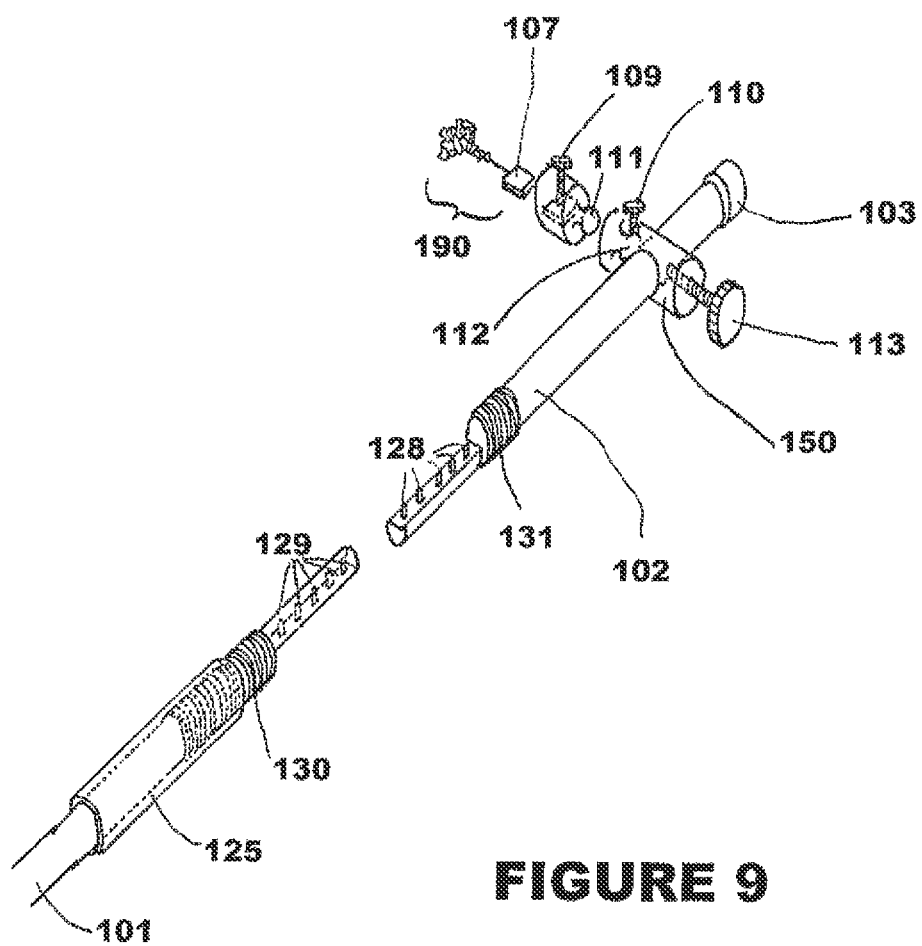
FIG. 9 illustrates an alignment tool ear tray according to one embodiment of the present invention.

FIG. 9 illustrates the ear-tray holding portion 102 of the alignment tool 100 and shows the ear impression tray 190 connected to the portion 102 via a male ball-joint means 111 to a female 112 both of which are part of the mounting means 150. The preferred material for taking ear impressions is a polyvinylsiloxane material, the same material widely used by dental professionals. Because the flow and consistency of the polyvinylsiloxane impression materials can vary, this type of material is preferred for both the mouth and ear impressions. The method taught by this invention for taking the ear impression will depend upon the requirements of the user or patient. The impression-taking technique may include flowing material into the pinna or having an ear loop wire which can be "picked-up" in the impression; other methods typically used by artisans in the art can also be used for a given situation.

Figure 12:
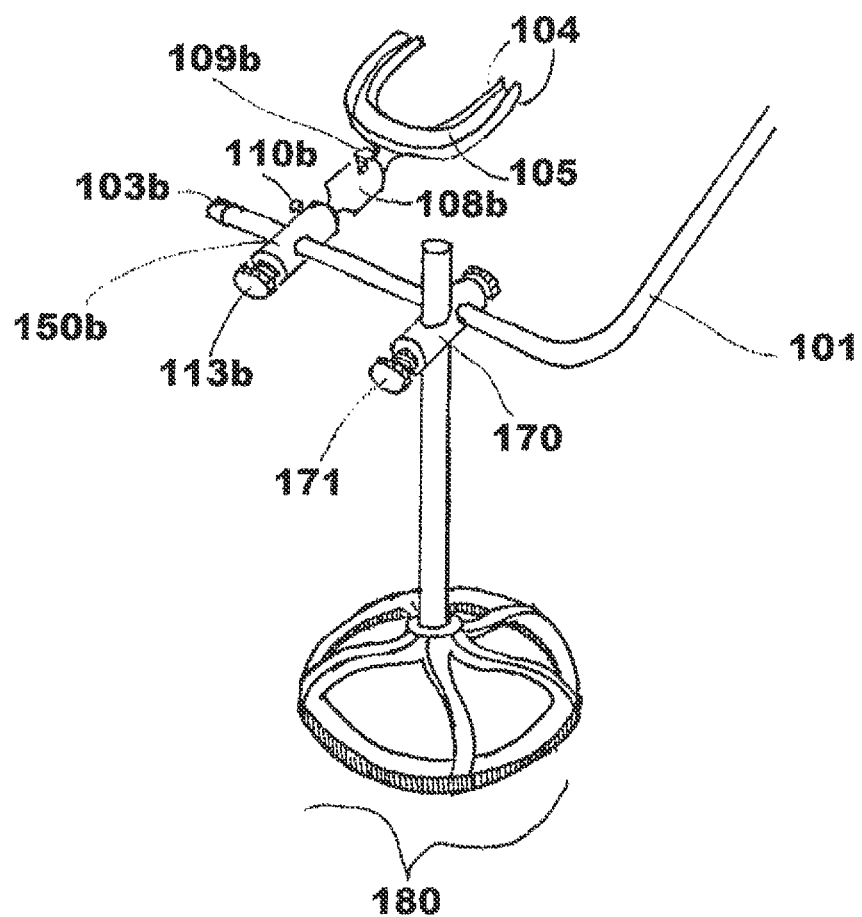
FIG. 12 illustrates a lab stand for holding the mouth-ear alignment tool during system analysis, design, and fabrication.

As shown in FIG. 9, a preferred construct of the alignment tool 100 is one in which portions 101 and 102 are extendably connected via extension means 128 and 129 and extension caps 130 and 131. The extension means can be any suitable means such as pins 128 and corresponding holes 129. The portions 101 and 102 also comprise end caps 103 which facilitate the assembly of mounting means 150 and 150b to the alignment tool 100. The endcaps are attached to the alignment tool 100 either through screw fitting or press-fit, and may or may not be of the same material as the alignment tool 100. The mouth impression portion 101 further comprises a laboratory stand mounting connector 170 from which the alignment tool 100 is detached during the anatomy recordation procedure as shown in FIG. 7. The stand mounting connector 170 is screwedly connected to the alignment tool 100 and has a pass through hole through which the stand rod 172 is also screwedly engaged as shown in FIG. 12.

Preferably, the alignment tool 100 is light-weight, rigid and non-magnetic. The light-weight is needed so as not to encumber or cause movement of either the mouth or ear impression after the alignment tool has engaged the impressions as shown in FIG. 7. Metallic tubing has been used in dental facebows and with the proper material selection, such as 303 stainless or aluminum alloy, such tubing may be appropriate. Ideally, the material should not be easily crushed, dented or deformed, as the various set-screws such as 113 and 170 could damage the alignment tool 100. In another embodiment, a solid plastic rod curved into the proper shape and drilled for pins and holes 128 and 129 could also be used.

The tray mounting means 150 and 150b for ball jointedly connecting the ear and mouth impression trays to the alignment tool 100 are preferably interchangeable and usable on either portion 101 or portion 102. Thus balls 111 and 111b, receptacles 108, set-screws 109, 110, 113, and the overall design and function of tray mounting means 150 is preferably same as 150b. The tray mounting means 150 and 150b can slide along portions 102 and 101 and when positioned approximately in the center of the mouth (or ear), are affixed by tightening the set screws 113 and 113b. Calibration scales (not shown) may optionally be provided along the portions 101 and 102 in slidable engagement with the tray mounting means 150 and 150b. Set screws 109 and 109b tighten the trays after they have been seated on the person, and screws 110 and 110b tighten the ball as the final adjustment before removing the alignment tool from the face to a reproducible location remote from the face.

The portions 101 and 102 are extendedly connected at disconnection sleeve 125 which comprise matable half-round rods 126 and 127 which project from portions 101 and 102 in an opposable manner respectively wherein retaining pins 128 project upward from the flat surface of 127, while pin holes 129 are drilled into 126 and are meant to receive the pins for calibrated extension and disconnection of the ear impression portion from the mouth impression portion. The disconnection sleeve 125 functions to stabilize portions 101 and 102 by engaging screw threads 130 and 131 which are at terminal ends of 101 and 102 respectively. Besides allowing for extendability of the alignment tool, the disconnection sleeve 125 allows the alignment tool to be removed from the person without distorting the impressions or ball-joint positions. By knowing which pin-holes were used, the alignment tool can then be re-assembled on the lab bench using the stand and methods exemplified in FIG. 12. Unlike a conventional dental facebow, in the present invention, when both mouth and ear impressions are in place, there is no path of removal without disturbing the ball-joints 150 and 150b except via the disconnection sleeve 125 which allows a calibrated disconnection of the alignment tool so that the delicate anatomical orientations captured by the impressions can be reproduced on a laboratory bench top. Following the teachings of this invention, the alignment tool 100 can further comprise calibration marks, or indeed other paths of disengagement from the face after measurement in a manner that would allow precise reproducibility of the measurements ex-user's face.

The first step in using the alignment tool 100 is to estimate the length of connected sections 101 and 102 of tool 100 and unscrew the disconnection sleeve 125 to set the pins 128 into their respective pin-holes 129. Then either a final mouth impression or an indexing impression using tray 105 is performed. That tray is then engaged to the alignment tool at set screw 109b and then set screws 110b and 113b loosened and tightened so that the tray mounting means 150 appears to be centered over the meatus of the external ear. Set screws 110 and 113 can also be lightly tightened.

The entire apparatus is then removed from the mouth. Using the ear impression tray 190, an ear impression is made and left in place with the ear impression tray element 107 projecting from the ear. Then the alignment tool is placed back into the mouth. Certain set screws are loosened as necessary so that the ear impression tray element 107 can tightly engage the connecting member 108. Then set screw 109 is tightened. Final adjustments are made to all set screws so that the entire mouth-ear alignment tool is rigid as shown in FIG. 7. Now disconnection sleeve 125 is carefully unscrewed exposing half-round rods 126 and 127. They are then separated, freeing portions 101 from 102. Without loosening any other screws, the alignment tool can be removed in two parts. First the ear impression is teased out of the ear, and then the mouth impression is removed.

Once off the face, the mouth-ear alignment tool is reconstituted at the proper pin setting and the disconnection sleeve 125 retightened. Then the lab stand mounting member 170 is attached at an arbitrary place so that it can be easily connected with the lab stand 180. See FIG. 12.

Figure 10:
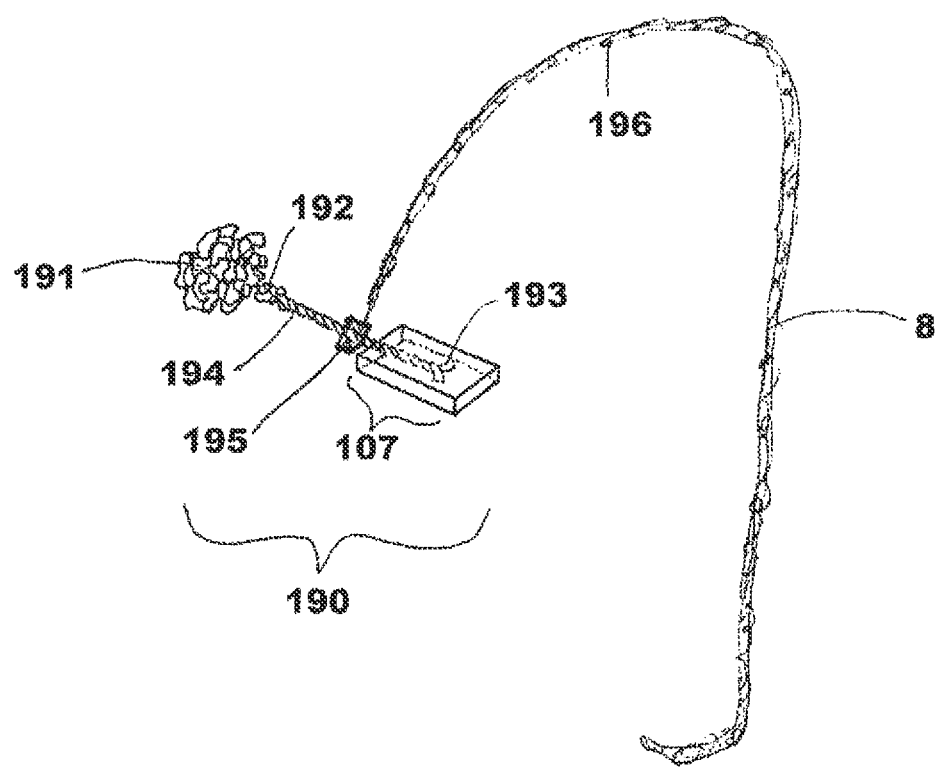
FIG. 10 illustrates an alignment tool's ear tray having an alternate ear loop.

FIG. 10 shows an ear tray 190 according to one embodiment of the present invention. The ear tray 190 comprises fine synthetic mesh material 192 which is similar to the mesh material used in disposable dental bite impression trays, and fine gauge, highly deformable wire 193 (e.g., stainless steel wire of 0.012 diameter). The two materials mesh 192 and wire 193 are twisted together and the terminal end is potted in a thermoplastic member 107 whose shape is designed to fit precisely into the female receptacle 108 on the mounting means 150. The other terminal end, 191, represents the "otoblock" which is known to artisans familiar with the art of taking ear impressions. The mesh and wire are so configured that the otoblock 191 is primarily entirely soft mesh and its position on the terminal end is established through twisting and bending of the soft thin wire 193. The twisted wire-mesh combination 194 and plastic "handle" of this tray member 107 are intended to project about 3-4 inches outside of the ear canal and pinna. This will place the tray member 107 in a favorable position to engage the ear tray mounting means 150 on the ear impression portion 102 of the alignment tool 100.

In another embodiment, the ear tray 190 may have an ear-loop 8 engaged to it. In this case, the ear-loop is a thin wire 196, about size 0.015 inches that is doubled (or tripled) wrapped around twisted wire-mesh combination 194 by the professional prior to taking the impression. The wire 196 is molded and verified for fit around the subject's ear. This earloop impression wire 196 may not necessarily be the final wire used as the earloop in the finished external unit 3. Instead this wire is used to index the position of where the final earloop should be placed. In the external unit 3 the earloop may be silicone-coated and/or constructed by methods known in the art. The point of engagement of wire 196 to twisted wire-mesh combination 194 is labeled 195. The precise location of the point of engagement 195 may be determined by the professional prior to taking the ear impression. The impression-wire earloop 196 will be held at 195 because of the physical and mechanical properties of the polyvinylsiloxane impression material that coats and covers the entire ear tray 190, except for the terminal area of tray member 107 that engages the alignment tool 100 through the mounting means 150.

In one embodiment, the methods of taking the ear impression are similar to those methods employed for taking the mouth impression. The tray is coated typically with an adhesive which helps the impression material stick to the tray. The professional places the otoblock 191 just beyond (medial) to the second bend of the ear canal. Impression material is then injected all around twisted wire-mesh combination 194 and may extend the material into the pinna area. If an impression earloop 196 is being used, then the impression material must be extended to include engagement point 195 (and perhaps a near part of 196). This is important because the earloop's position and orientation relative to the tray member 107 should be captured by the impression material so that it can be reproduced later at the laboratory.

Figure 11:
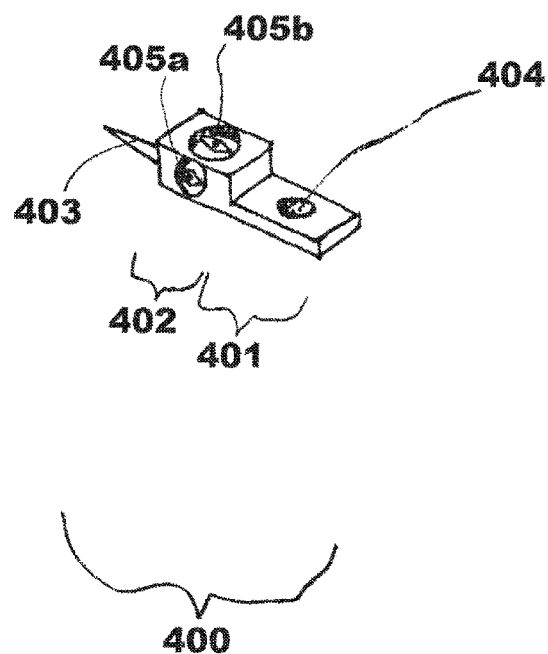
FIG. 11 illustrates a pointer usable for external units such as shown in FIG. 3.

FIG. 11 more fully illustrates the pointer 400 described above in the discussion of the self-customized embodiment of an external unit 3. Self-customization using the alignment tool 100 is to be distinguished from the technician aided customization which is the preferred modality of use of the alignment tool 100. Generally, self-customization will be used for "Send-mode" applications where antenna orientations or changes in orientation of the external antenna 6 is difficult for the user to know, particularly without a side-tone (and normal hearing capability by the user). When the user is transmitting their own voice, for example, should the optimum orientation between internal antenna 5 and external antenna 6 become altered, there is a significant chance of increase noise in the signal. Without a side-tone, the user cannot know about this misalignment of antennas, nor importantly, can the user re-align the antennas to the optimum linear orientation without use of this invention. Without the invention, the user is relegated to "trial and error" method of moving the external antenna 6. In many military-type high noise environments, such "trial and error" may not be possible. Use of the pointer presumes that the internal unit 4 and internal antenna 5 will not change position largely because that unit 4 has already been customized, or self-customized and is affixed rigidly against a tooth.

Pointer 400 resembles the ear tray in that the size and shape of block 401 is the same dimensions as the ear tray member 107. Like 107, the entire pointer 400 is non-metallic plastic, except for compass needles 405a and 405b. Area 401 engages the ear tray mounting means 150 just as tray member 107 would in the technician aided modality and is locked into the mounting means 150 by the same set-screw 109 as is used in the preferred embodiments described in FIGS. 8 and 9. Set-screw 109 locks pointer 400 at depression area labeled 404. Area 402 of the block contains two compass needles mounted at right angles; the compasses are labeled 405a and 405b. These two different compasses correspond to two planes of the skull; front-back (horizontal plane or "x"-plane) and up-down (vertical or "y"-plane). A non-metallic pointer-needle 403 is centered and fixed within the pointer 400 as shown in FIG. 11.

The self-customized modality using the pointer 400 is as follows. The alignment tool 100 is modified for length at pins 127 and pin holes 128 and the portions 101 and 102 secured by disconnection sleeve 125. Also as is done in the technician-aided modality, an impression or index impression is taken of the teeth using mouth tray 105. The pointer 400 is tightened into mounting means 150 using set-screw 109 (tightening into 404), but the other set-screws 110 and 113 are not tightened.

The alignment tool is then set aside and the subject obtains a previously built internal unit. This unit may have been made from a professionally made mouth impression or from a self-made impression of the teeth. A small mouth-safe disk magnet is placed over the internal antenna 5 using wax, glue or some adhesive. The magnet is positioned on the buccal side of the internal unit 4 so that the magnet is at the point of optimum reception/transmission efficiency for its paired external antenna 6. In a loop-type design, for example, the magnet would be placed parallel to the plane in the center of the loop. It is understood that the point of optimum reception/transmission efficiency is known by the system designers or manufacturer. Ideally this "optimum point" is the theoretical center of co-planar magnetic fields created by a pair of antennas ideally co-located, one inside the mouth and the other outside the mouth, at a distance of less than 6 inches. As a service to the user prior to sale, the manufacturer may indicate this location on the internal unit 4 with a dot or depression. They also should indicate the "tilt" of the loop and so that a user can replicate that tilt on the buccal surface of the internal unit 4. Thus a small disk magnet could easily "drop-into" the ideal orientation of the antenna 5 on this unit. After the magnet has been properly attached to the buccal surface of the internal unit 4, it is re-seated into the mouth.

The alignment tool 100 is placed back into the mouth, using the teeth index taken previously. The mounting means 150 is rotated and slid back and forth along portion 102 until the pointer needle 403 is parallel to the two compass needles, 405a and 405b. At that moment, the set-screws 110 and 113 are tightened. The external unit 3 then is placed into or onto the ear. The external antenna 6, wherever it is on that unit, can then be moved, rotated, deflected, etc. so that the antenna is aligned to the area on the cheek pointed to by pointer needle 403. In addition, particularly if it is a loop design, this antenna should be aligned perpendicular to the pointer-needle 403, and centered. The external antenna 6 thus can achieve the optimum location on the skull for reception/transmission relative to the internal antenna 5 of a low-power signal device. Once the location for external antenna 6 is determined, it can be held in that correct orientation with skin tape, helmet straps, wax, self-customized ear plugs, ear hooks, ear loops, putty, or any combination of related means which ultimately hold the external unit 3 in this determined position.

FIG. 12 is the lab stand for holding the mouth-ear alignment tool during system analysis, design, and fabrication. The stand 180 is any suitable stand and can be a basic element to dental alignment tool laboratory transfer technique. It is understood by a skilled artisan in this art that the material of the stand and the alignment tool 100 can be any suitable non-magnetic material. As taught, after the mouth and ear impressions have been made, the representations of the precise mouth and ear anatomy can be placed on the stand 180 and the spatial relationships studied. The stand mounting connector 170 is used to attach alignment tool 100 to the laboratory stand 180. In a preferred embodiment, after the mouth-ear impressions are taken and the spatial relationships recorded, the stand mounting connector 170 is attached to the alignment tool along the length of mouth impression portion 101. It is then secured to the stand 180 by set-screw 171. Should additional support be needed for the (heavy) models of the oral and aural anatomy, boxes and other jigs are an obvious solution. It is also possible that additional means might be needed in the laboratory to prevent slippage of the set-screws 109, 110, 113 and 109b, 110b, 113b, such means being clamps, jigs, glues, are all encompassed by the invention.

According to another embodiment, data corresponding to the anatomy of and spatial orientation between the oral and aural anatomy is obtained through the use of imaging mechanisms, such as systems which utilize ionizing radiation (e.g., cone beam tomography, and 3-D x-rays), or non-ionizing systems (e.g., magnetic resonance imaging, and optical systems/laser techniques such as emission re-absorption laser induced fluorescence (ERLIF) techniques.

As known in the art, such imaging technology may be utilized for dental implant placement, skull and brain surgery, and other medical procedures where knowledge of three-dimensional anatomy is beneficial. Various imaging techniques are known for rendering in three dimensions the human anatomy, including volume measurements. For example, see Chenin D. L. et al. (2009), "*Dynamic cone-beam computed tomography in orthodontic treatment*," J. Clin. Orthod., 43:507-12; Periago D. R. et al. (2008), "*Linear accuracy and reliability of cone beam CT derived 3-dimensional images constructed using an orthodontic volumetric rendering program*," Angle Orthod., 78:387-95. Magnetic resonance imaging is another software-based technique that can be used to measure the distance between landmarks placed within or near to the ear canal and to another landmark placed within the oral cavity. Another different imaging technique uses optical means (e.g., see U.S. Patent Publication No. 2010/0067756), such as ERLIF techniques. However, conventional ERLIF techniques provide for the separate recording of data corresponding to the ear canal or the oral structures, and do not associate or link the anatomical information from two sites for purposes of obtaining distance or angle measurements between designated landmarks (such as in the mouth or ear).

According to the present invention, such imaging systems may be used to collect data usable by computer software that precisely models the skull and/or head (or specific parts thereof) in three dimensions. Conventional CAD/CAM techniques for three-dimensionally modeling data recorded from imaging system are known in the art (e.g., see software and techniques available from Align Technologies, 3M, and Patterson), and have been utilized in the dental field to model the relationship between the upper and lower jaws, model the bite, and for the fabrication of dental appliances (orthodontic) and prostheses.

Skull and head imaging systems and the associated computer modeling software are utilized in the present invention to determine optimum antenna design, alignment, and antenna placement both intra-orally and extra-orally. The ideal parameters of a system antenna design in an air medium for a given frequency of carrier signal, distance between loop antennas, size and shape of antenna, etc. may be readily calculated by one skilled in the art. These ideal parameters will be modified based on the collected anatomical data from the imaging system and other factors such as power available from an acceptably sized battery, losses or noise caused by signal transmission through water/tissue, etc.

Once the parameters which govern the antenna system design have been modeled, the external unit and internal unit can be built using an appropriate technique, such as CAD/CAM. That the antenna system has been optimized for the given anatomy can be verified by a technician on a laboratory bench top. For example, radio signal strength may be measured in the receiver unit when the assemblies are attached to and held in position by the alignment tool 100 (without the impression trays, given such trays are not necessary for this embodiment) and laboratory stand 180, such as shown in FIG. 12. The measured radio signal strength may then be compared to the calculated ideal Lorentz Force (F), wherein:

$$F=q[E+(v \times B)],$$

and/or as compared to the calculated induced electromotive force (EMF) under Faraday's Law, wherein:

$$EMF := \oint (E+v \times B)$$

Preferably, the alignment tool 100 and laboratory stand 180 are formed from a material that will not interfere with the signal transmissions of the antennas, as noted above. For example, the alignment tool 100 and stand 180 may be formed from plastic, or some other non-metal, and low or non-conductive material.

Alternatively or in addition, the signal strength and noise levels (SNR) may be measured by using a separate test or auxiliary antenna, a gaussmeter, or a magnetometer, or a Hall-sensor, which may be attached to the laboratory stand 180 and/or at a location proximate to the internal unit (or receiver) for measuring signal strength. By utilizing the test antenna and/or field or signal strength measuring devices, the possibility that other electronic issues might have occurred within the receiver unit (e.g., such as a faulty battery contact) may be identified and corrected. Optimal design and alignment of the receiver unit relative to the transmitter unit may thereby be confirmed in the laboratory. Later, when the receiver unit is positioned on and/or attached to the user (e.g., in a fixed position in the mouth of the user), the user can be assured that the antennas have been optimally positioned and aligned for repeatable signal strength and clarity.

Using such imaging techniques in combination with ideal antenna calculations, the actual antenna pair may be computer modeled in the laboratory. Thus the exact placement and orientation of the antennas and their associated internal and external units in and/or on the skull may be designated before the customized system is built and delivered to the user. Through knowledge of the spatial anatomy of both the oral cavity and external ear as gleaned from the disclosed imaging techniques, both parts of the transmitter/receiver system can be properly and efficiently oriented and aligned a priori.

For optimal and consistent in-situ device performance over time, given that there will be repeated removal and replacement of the device by the user, the device (and associated antenna pair) should be securable on the oral and aural structures. With proper fixation of the device (and associated antennas), whereby slippage, movement and/or rotation are eliminated or minimized, then the optimal device performance can be maintained. For example, in a preferred embodiment of the hearing augmentation system of the present invention, the external antenna and associated external unit is preferably secured within the ear canal for a snug fit therein, such as provided by a completely-in-canal (CIC-type) hearing aid. The mouth unit with the internal antenna is located and oriented in a fixed position via a semi-rigid attachment mechanism, such as a bracket, band, claw or other member for securing the internal unit to the tooth or teeth.

Other pairing and alignment methods and mechanism may alternatively be employed utilizing collected imaging data and associated computer modeling software. For example, the extra-oral assembly may be secured to a user's head at a position outside of the ear canal, in which case the external ear or pinna three-dimensional anatomy data may be appropriated collected via the imaging technologies noted herein. Similarly, the external landmark may be affixed with skin tape in a position that closely approximates the intended position should the user be wearing a helmet or head strap.

Further, utilizing the disclosed methods and systems, a database of physical properties relevant to signal transmission through human skull tissue will be created. For example, relevant physical properties may include, but are not limited to, the size of the skull, the distance between the antenna pairing, the density and quality of bone, the age of the patient, whether there are "foreign materials" such as implants within the skull, etc. The database may further reflect power or signal loss, such as the power ratio in decibels (dB) of the measured power referenced to one milliwatt (mW) and/or signal distortion and interference as caused by any of the above physical parameters. As data is collected over time, the database will allow for more efficient computer modeling and design of the antenna pair.

Figure 13:
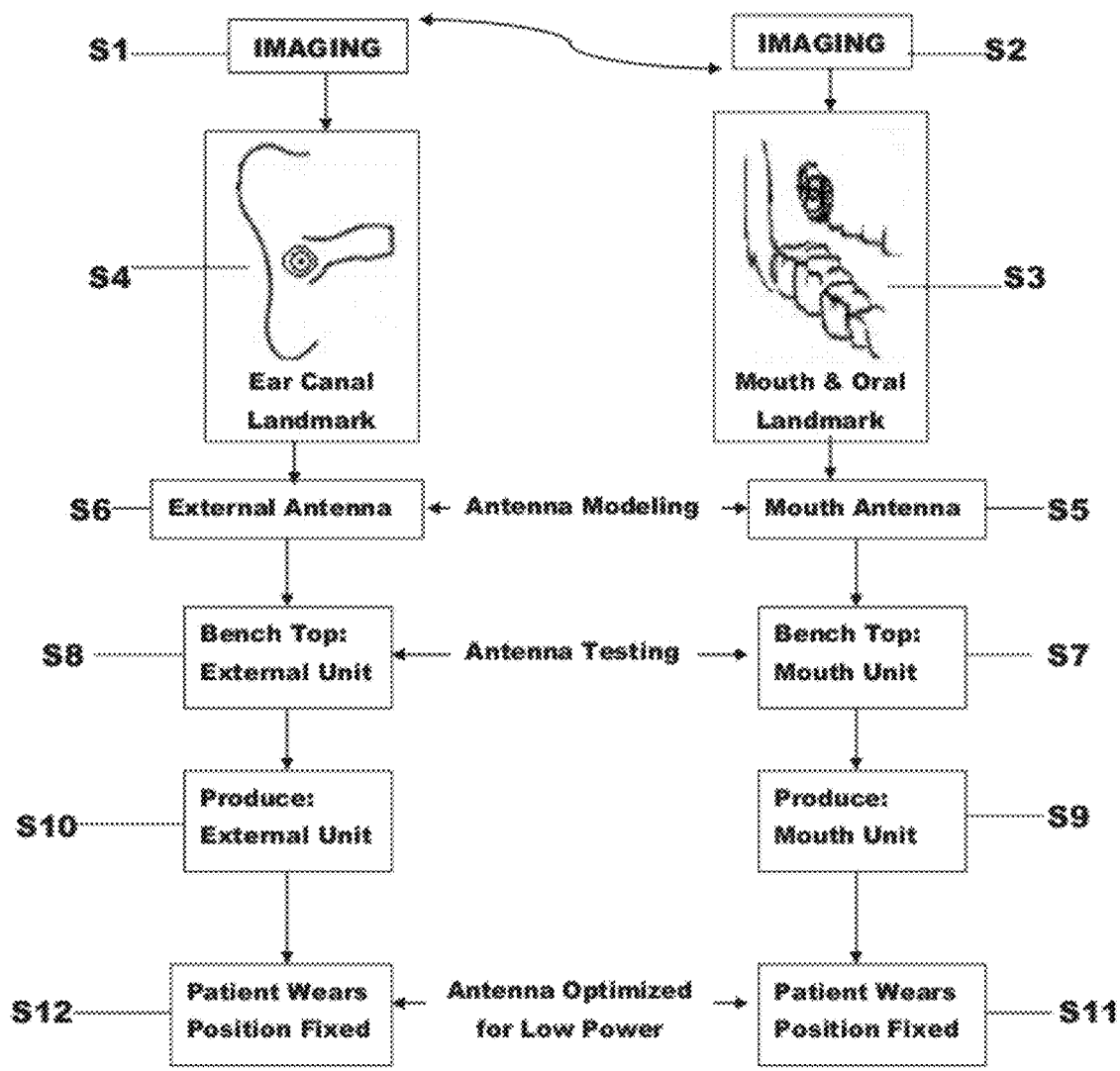
FIG. 13 is a flowchart of a method of optimizing internal and external antennas of a hearing augmentation system according to an embodiment of the present invention.

Thus, anatomical data for placement, design and orientation of the extra- and intra-oral hearing augmentation assemblies may be rapidly collected and maintained using the various imaging technologies disclosed herein along with associated computer software for processing the collected data. A flowchart showing an exemplary method of optimizing internal and external antennas of a hearing augmentation system is shown in FIG. 13. The anatomical features and 3-D configuration of desired portions of a patient's ear are measured and recorded via imaging technology at S1. The anatomical features and 3-D configuration of the patient's mouth are also measured and recorded via imaging technology at S2. The spatial relationship between landmarks within the oral cavity (oral landmark (OL)), and landmarks in or near the ear canal (ear landmark (EL)) are determined via the imaging device and associated data processing software at S3 and S4, respectively.

The anatomical volumes of the oral and aural cavities are determined, so that the optimum size and shape of the internal and external antennas may be modeled at S5 and S6. The antennas are configured so that they comfortably fit within or in proximity to the subject cavities.

The modeled internal antenna and external antenna are then secured to an alignment tool (e.g., alignment tool 100) or other holding device so that they are oriented relative to each other as they would be when secured to the patient or user. The antennas may then be tested for optimal signal transmission at S7 and S8. As noted above, the optimum configuration of the antenna pair is based upon the transmission carrier-frequency band, and in light of theoretical and known interactions of the signal transmission between the skull and head tissue medium (e.g., water, muscle, bone), as well as other considerations such as distance between the antennas, available battery power and/or drain for a given system, proximity of other users at eth same carrier frequency, etc.

Based on the determined optimal configuration, tilt and orientation of the antennas relative to each other (and in light of the skull and head data collected via the imaging device), the internal unit is constructed at S9 and the external unit is constructed at S10. The internal and external units may then be fixedly attached to the patient or user at S11 and S12, with the antennas optimized for low power signal transmission.

In one embodiment, a maxillofacial cone beam computed tomography (CBCT) imaging system may be utilized. The cost of three-dimensional cone beam systems is sufficiently low, and the resulting three-dimensional image data collected is sufficiently accurate for use with the present invention. Further, such cone beam systems produce minimal radiation exposure to the user during data collection. Thus, they are relatively safe for the user and/or patient. For most applications, the field of view or scan volume area necessary for such imaging techniques is limited to primarily the jaws and ears, given that is where the transmitter and receiver assemblies are positioned and secured on the user.

For cone beam imaging and/or other imaging technologies, it may be appropriate to utilize a contrast solution agent during data collection (e.g., see Omnipaque (GE Healthcare)). Other conventional imaging techniques may additionally or alternatively utilized chemical mediums, solutions and/or gels to improve the brightness, coloration, contrast, and/or clarity of the image of the desired structure.

According to an exemplary method of anatomical data collection, such as via a CBCT imaging system, a "dummy" mouth unit may be placed into a retaining means (e.g., a band, bracket, claw, etc.). The dummy unit has a configuration generally or substantially similar to the internal unit to be designed and placed within the mouth of the user. The dummy unit is secured to the patient via the bracket prior to the patient undergoing the CBCT (or other imaging process). This is because the bracket and the patent's tooth have a specific tilt, and the tilt is not known prior to the CBCT. The dummy unit contains a radiopaque coil (or radio opaque object such as a flat washer) of standardized and relatively small dimensions (e.g., having a thickness of about 0.25 mm, an internal diameter of about 1.5 mm, and an outer diameter of about 2.5 mm). These dimensions may be standardized. The software models the appropriate anatomy and utilizes data from the detected coil (or flat washer) as the oral landmark (OL). Preferably, the dummy unit is disposable, and may for example be formed of plastic or some other material that is relatively or primarily radiolucent except for its outline. The dummy unit contains a high-contrast but mouth safe coiled metal or flat washer that serves as the oral landmark (OL) representing the intra-oral antenna.

Figure 14:
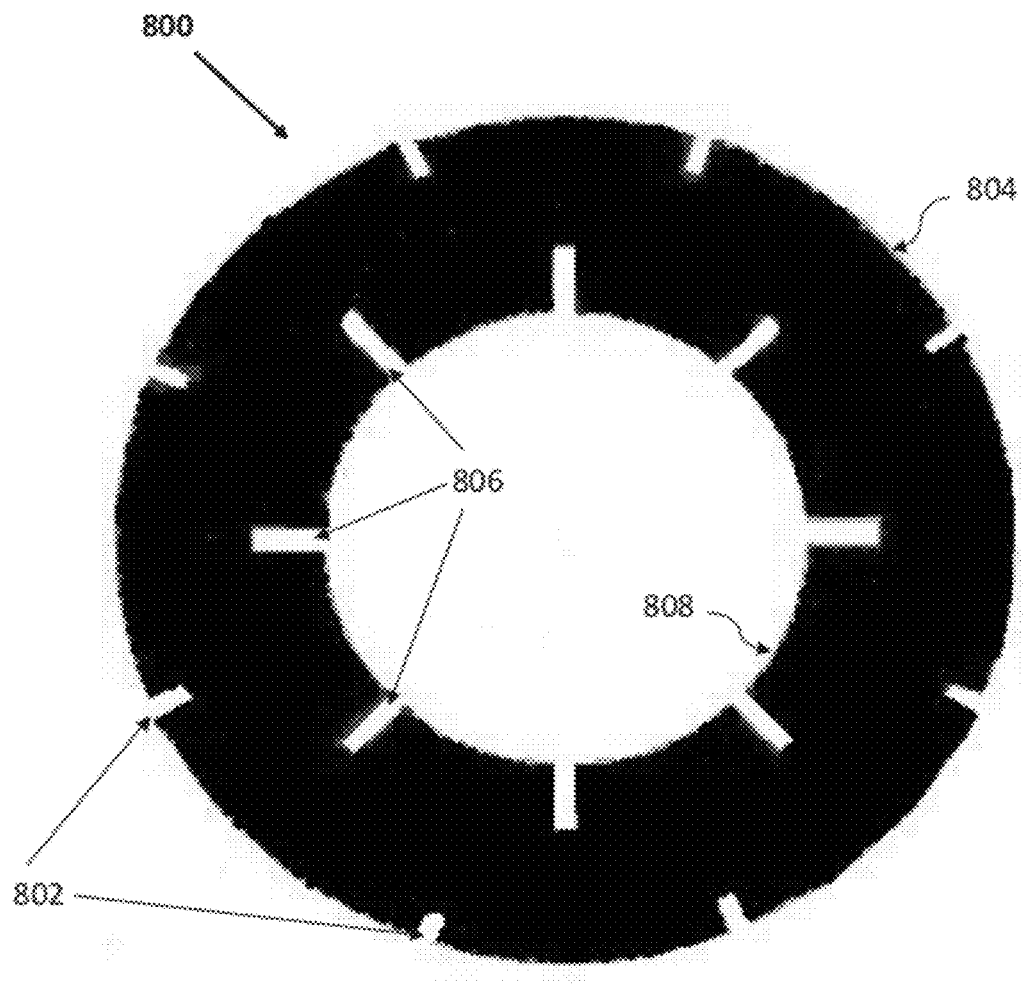
FIG. 14 illustrates a dummy washer configured as a flat washer for use in a dummy unit according to the present invention.

Thus, the coil or washer represents the antenna. An exemplary washer member 800 for use in the dummy unit is shown in FIG. 14. The washer member 800 or "dummy antenna" aids in reconstructing the 3-D image based on the collected anatomical data by the imaging technology. For example, the precise configuration and orientation of dummy antennas in the internal and external units are detected by the imaging equipment, such as for example a CBCT imaging system. The data is then processed by the associated software, which creates a 3-D model of the users head. The configuration and precise orientation of the dummy antennas relative to each other and relative to the user's head are thereby determined.

In addition, size restraints for the antennas are also determined. The resulting internal and external units (and thus associated antennas) are placed preferably in soft-tissue and cartilaginous areas of the user's head. For example, the external unit may be positioned and secured at the entrance to the user's auditory canal; the internal unit is positioned within the mouth of the user, preferably in the retromolar area (i.e., the area high inside the check behind the last maxillary molar).

The washer (e.g., washer 800) preferably has specific dimensions that may be "set" or programmed into the software. For example, the open hash mark areas or indents 802 extending into the outer periphery 804, and the open hash mark areas or indents 806 extending into the inner edge 808 preferably have predetermined and specific lengths and spacing. Further, the thickness of the washer 800 is known. Given the specific dimensions of the washer 800 are known, the precise tilt of both antennas in-situ is detected by the CBCT and determined and shown by the processed data via the modeling software. Further, since the washer 800 is placed at the opening to the external canal of the ear, that anatomical dimension can be read precisely by the associated CBCT software.

It should be understood that the dummy antennas may have alternative configurations, such as rectangular, square, triangular or oval plates. Other geometric configurations may alternatively be employed. However, the dummy antenna preferably has a configuration which allows for its tilt to be identified during the imaging process.

The ear canal may be swathed with a contrast solution in order to capture greater detail of the ear canal volume and precise anatomical configuration. Although the disposable dummy plastic unit may not fit snuggly like a CIC-type hearing aid, the dummy plastic unit functions like the mouth dummy unit and may be placed in the ear. This ear dummy unit preferably includes a contrasting metal coil which will serve as the ear landmark (EL) and represents the first approximation of the position for the extra-oral antenna.

Alternatively, the ear dummy unit may be configured as a flat washer or have another geometric configuration as noted above.

Other imaging contrasting techniques may alternatively be used for the ear canal, such as a balloon that will fill the canal and make for a better image of the volume.

In another embodiment, anatomical data is collected via a laser imaging system, such as an ERLIF imaging system, and processed via associated software. For an ERLIF imaging system, a hardware means is utilized to link and establish the three-dimensional coordinates between the mouth image and ear image. For example, a mechanical linkage may be similar to the alignment tool 100 described above. The mechanical linkage utilizes a fixed-distance L-shaped member to establish the horizontal x-plane between the protruding tips of the two trays (mouth and ear). The y-plane and z-plane axis may be determined either through imaging the tips of each tray respectively or through electronic contacts on the tips of each tray.

Accordingly, in the system utilizing laser imaging technology, through the use of the mouth and ear images, the resulting data may be processed via conventional software associated with the imaging data to match and align the antennas of the intra- and extra-oral assemblies in consideration of the anatomical constraints and optimal frequency of the wireless signal transmission. Further, space limitations may dictate the battery size and power availability of the mouth-worn (intra-oral) system. In addition, cosmetic considerations may factor into the design and placement of the external antenna and/or assembly.

For other applications, regulatory restraints may dictate the transmission band available. Thus, the configuration of the antenna is determined by transmission frequency allowed by the regulatory agency. For example, for military applications, such as when used by soldiers closely co-located and/or seeking covert transmission or on-the-move usage, the overall system design including antenna selection should accommodate such specialized situations. Hence, the optimal design and positioning of the paired antenna is achieved through the disclosed methods and systems.

It will be apparent to those skilled in the art that various modifications and variations can be made to the present invention without departing from the spirit or scope of the invention. Modification of the above-described assemblies and methods for carrying out the invention, combinations between different variations as practicable, and variations of aspects of the invention that are obvious to those of skill in the art are intended to be within the scope of the claims. The drawings here presented are for illustrative purposed only and are no necessarily drawn to scale. Thus, it is intended that the present invention cover the modifications and variations of this invention provided they come within the scope of the appended claims and their equivalents. Accordingly, the invention is not limited by the embodiments described above which are presented as examples only but can be modified in various ways within the scope of protection defined by the appended patent claims. All references cited in this specification are herein incorporated by reference in their entireties.

What is claimed is:

1. A method of aligning antennas of an intra-oral and extra-oral electronic wireless device, comprising the steps of:
    recording three-dimensional anatomical data of at least a portion of an oral cavity of a subject utilizing an imaging device;
    recording three-dimensional anatomical data of at least a portion of an external ear of the subject utilizing the imaging device;
    determining a spatial relationship between a landmark in the oral cavity and a landmark in or near the external ear;
    modeling an intra-oral antenna based upon the recorded anatomical data of the oral cavity; and
    modeling an extra-oral antenna based upon the recorded anatomical data of the external ear, wherein the intra-oral and extra-oral antennas are configured and oriented relative to each other for optimal signal transmission based upon the recorded anatomical data of the oral cavity and external ear.

2. The method of claim 1, wherein the imaging device is a non-ionizing radiation system.

3. The method of claim 1, wherein the imaging device is selected from the group consisting of an X-ray imaging system, a computed tomography imaging system, a magnetic resonance imaging system, and an optical imaging system.

4. The method of claim 1, comprising the further steps of:
    constructing an internal unit configured to be disposed within the oral cavity of the subject, the intra-oral antenna coupled to the internal unit; and
    constructing an external unit configured to be disposed within or proximate to the ear of the subject, the extra-oral antenna coupled to the external unit.

5. The method of claim 4, wherein the intra-oral and extra-oral antennas are fixedly and spatially oriented relative to each other for optimal gain and polarization when the internal and external units are disposed within or upon the subject.

6. The method of claim 1, wherein the intra-oral antenna has a first angular orientation, and the extra-oral antenna has a second angular orientation relative to the first angular orientation, wherein the signal transmission is optimized when the intra-oral and extra-oral antennas are orientated in the first and second angular orientations, respectively.

7. The method of claim 1, wherein the imaging device is an ionizing radiation system.

* * * * *